(12) United States Patent
Deisseroth et al.

(10) Patent No.: US 8,729,040 B2
(45) Date of Patent: May 20, 2014

(54) CELL LINE, SYSTEM AND METHOD FOR OPTICAL CONTROL OF SECONDARY MESSENGERS

(75) Inventors: Karl Deisseroth, Palo Alto, CA (US); Raag D. Airan, Washington, DC (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 12/993,605

(22) PCT Filed: May 29, 2009

(86) PCT No.: PCT/US2009/045611
§ 371 (c)(1),
(2), (4) Date: Jan. 20, 2011

(87) PCT Pub. No.: WO2009/148946
PCT Pub. Date: Dec. 10, 2009

(65) Prior Publication Data
US 2011/0112179 A1 May 12, 2011

Related U.S. Application Data

(60) Provisional application No. 61/057,108, filed on May 29, 2008.

(51) Int. Cl.
*G01N 33/53* (2006.01)
(52) U.S. Cl.
USPC ....... 514/44 R; 435/455; 435/6.17; 536/23.4; 607/88
(58) Field of Classification Search
CPC ........... C07K 2319/00; C07K 2319/60; C07K 2319/70; C07K 14/723; G01N 2021/00
See application file for complete search history.

(56) References Cited

U.S. PATENT DOCUMENTS

| | | |
|---|---|---|
| 2,968,302 A | 1/1961 | Fry et al. |
| 3,131,690 A | 5/1964 | Innis et al. |
| 3,499,437 A | 3/1970 | Balamuth et al. |
| 3,567,847 A | 3/1971 | Price |
| 4,343,301 A | 8/1982 | Indech |
| 4,559,951 A | 12/1985 | Dahl et al. |
| 4,616,231 A | 10/1986 | Autrey et al. |
| 4,865,042 A | 9/1989 | Umemura et al. |
| 4,879,284 A | 11/1989 | Lang et al. |
| 5,032,123 A | 7/1991 | Katz et al. |
| 5,041,224 A | 8/1991 | Ohyama et al. |
| 5,082,670 A | 1/1992 | Gage et al. |
| 5,249,575 A | 10/1993 | Di Mino et al. |
| 5,267,152 A | 11/1993 | Yang et al. |
| 5,290,280 A | 3/1994 | Daikuzono et al. |
| 5,330,515 A | 7/1994 | Rutecki et al. |
| 5,460,950 A | 10/1995 | Barr et al. |
| 5,460,954 A | 10/1995 | Lee et al. |
| 5,470,307 A | 11/1995 | Lindall |
| 5,495,541 A | 2/1996 | Murray et al. |
| 5,520,188 A | 5/1996 | Hennige et al. |
| 5,527,695 A | 6/1996 | Hodges et al. |
| 5,550,316 A | 8/1996 | Mintz |
| 5,641,650 A | 6/1997 | Turner et al. |
| 5,703,985 A | 12/1997 | Owyang et al. |
| 5,722,426 A | 3/1998 | Kolff |
| 5,738,625 A | 4/1998 | Gluck |
| 5,739,273 A | 4/1998 | Engelman et al. |
| 5,741,316 A | 4/1998 | Chen et al. |
| 5,755,750 A | 5/1998 | Petruska et al. |
| 5,756,351 A | 5/1998 | Isacoff et al. |
| 5,782,896 A | 7/1998 | Chen et al. |
| 5,795,581 A | 8/1998 | Segalman et al. |
| 5,807,285 A | 9/1998 | Vaitekunas et al. |
| 5,939,320 A | 8/1999 | Littman et al. |
| 6,134,474 A | 10/2000 | Fischell et al. |
| 6,161,045 A | 12/2000 | Fischell et al. |
| 6,253,109 B1 | 6/2001 | Gielen |
| 6,303,362 B1 | 10/2001 | Kay et al. |
| 6,334,846 B1 | 1/2002 | Ishibashi et al. |
| 6,336,904 B1 | 1/2002 | Nikolchev |

(Continued)

FOREIGN PATENT DOCUMENTS

| | | |
|---|---|---|
| EP | 1 334 748 | 8/2003 |
| JP | 2006-295350 | 10/1994 |
| WO | WO 01-25466 | 4/2001 |
| WO | WO-03/016486 A2 * | 2/2003 |
| WO | WO 03-040323 | 5/2003 |
| WO | WO 03-084994 | 10/2003 |
| WO | WO 03-102156 | 12/2003 |
| WO | WO 2007-024391 | 3/2007 |
| WO | WO 2007-131180 | 11/2007 |
| WO | WO2009/119782 | 10/2009 |

(Continued)

OTHER PUBLICATIONS

Zita A. Peterlin et al., Optical probing of neuronal circuits with calcium indicators. PNAS Mar. 28, 2000 vol. 97 No. 7 3619-3624.*
Jong-Myoung Kim et al., Light-Driven Activation of beta2-Adrenergic Receptor Signaling by a Chimeric Rhodopsin Containing the beta2-Adrenergic Receptor Cytoplasmic Loops. Biochemistry 2005, 44, 2284-2292.*
Natochin M et al., Probing rhodopsin-transducin interaction using *Drosophila* Rh1-bovine rhodopsin chimeras. Vision Res. Dec. 2006;46(27):4575-81.*

(Continued)

*Primary Examiner* — Scott Long
*Assistant Examiner* — Arthur S Leonard
(74) *Attorney, Agent, or Firm* — Paula A. Borden; Bozicevic, Field & Francis LLP.

(57) ABSTRACT

A variety of methods, devices and compositions are implemented for light-activated molecules. One such method is implemented for generating secondary messengers in a cell. A nucleotide sequence for expressing a chimeric light responsive membrane protein (e.g., rhodopsin) is modified with one or more heterologous receptor subunits {e.g., an adrenergic receptor (alpha1, Beta2)}. The light responsive membrane protein is expressed in a cell for producing a secondary messenger in response to light.

22 Claims, 5 Drawing Sheets

(56) References Cited

U.S. PATENT DOCUMENTS

| | | |
|---|---|---|
| 6,364,831 B1 | 4/2002 | Crowley |
| 6,377,842 B1 | 4/2002 | Pogue et al. |
| 6,436,708 B1 | 8/2002 | Leone et al. |
| 6,473,639 B1 | 10/2002 | Fischell et al. |
| 6,480,743 B1 | 11/2002 | Kirkpatrick et al. |
| 6,489,115 B2 | 12/2002 | Lahue et al. |
| 6,497,872 B1 | 12/2002 | Weiss et al. |
| 6,506,154 B1 | 1/2003 | Ezion et al. |
| 6,536,440 B1 | 3/2003 | Dawson |
| 6,551,346 B2 | 4/2003 | Crossley |
| 6,567,690 B2 | 5/2003 | Giller et al. |
| 6,597,954 B1 | 7/2003 | Pless et al. |
| 6,609,020 B2 | 8/2003 | Gill |
| 6,631,283 B2 | 10/2003 | Storrie et al. |
| 6,632,672 B2 | 10/2003 | Calos |
| 6,647,296 B2 | 11/2003 | Fischell et al. |
| 6,685,656 B1 | 2/2004 | Duarte et al. |
| 6,686,193 B2 | 2/2004 | Maher et al. |
| 6,721,603 B2 | 4/2004 | Zabara et al. |
| 6,729,337 B2 | 5/2004 | Dawson |
| 6,780,490 B1 | 8/2004 | Tanaka et al. |
| 6,790,652 B1 | 9/2004 | Terry et al. |
| 6,790,657 B1 | 9/2004 | Arya |
| 6,805,129 B1 | 10/2004 | Pless et al. |
| 6,810,285 B2 | 10/2004 | Pless et al. |
| 6,889,085 B2 | 5/2005 | Dawson |
| 6,921,413 B2 | 7/2005 | Mahadevan-Jansen et al. |
| 6,969,449 B2 | 11/2005 | Maher et al. |
| 6,974,448 B2 | 12/2005 | Petersen |
| 7,045,344 B2 | 5/2006 | Kay et al. |
| 7,091,500 B2 | 8/2006 | Schnitzer |
| 7,144,733 B2 | 12/2006 | Miesenbock et al. |
| 7,175,596 B2 | 2/2007 | Vitek et al. |
| 7,191,018 B2 | 3/2007 | Gielen et al. |
| 7,211,054 B1 | 5/2007 | Francis et al. |
| 7,298,143 B2 | 11/2007 | Jaermann et al. |
| 7,313,442 B2 | 12/2007 | Velasco et al. |
| 7,603,174 B2 | 10/2009 | De Ridder |
| 7,610,100 B2 | 10/2009 | Jaax et al. |
| 7,613,520 B2 | 11/2009 | De Ridder |
| 7,686,839 B2 | 3/2010 | Parker |
| 7,824,869 B2 | 11/2010 | Hegemann et al. |
| 8,398,692 B2 | 3/2013 | Deisseroth et al. |
| 2002/0094516 A1 | 7/2002 | Calos et al. |
| 2002/0155173 A1 | 10/2002 | Chopp et al. |
| 2003/0026784 A1 | 2/2003 | Koch et al. |
| 2003/0040080 A1 | 2/2003 | Miesenbock et al. |
| 2003/0050258 A1 | 3/2003 | Calos |
| 2003/0097122 A1 | 5/2003 | Ganz et al. |
| 2003/0104512 A1 | 6/2003 | Freeman et al. |
| 2003/0125719 A1 | 7/2003 | Furnish |
| 2003/0204135 A1 | 10/2003 | Bystritsky |
| 2003/0232339 A1 | 12/2003 | Shu et al. |
| 2004/0034882 A1 | 2/2004 | Vale et al. |
| 2004/0039312 A1 | 2/2004 | Hillstead et al. |
| 2004/0122475 A1 | 6/2004 | Myrick et al. |
| 2004/0203152 A1 | 10/2004 | Calos |
| 2005/0058987 A1 | 3/2005 | Shi et al. |
| 2005/0119315 A1 | 6/2005 | Fedida et al. |
| 2005/0124897 A1 | 6/2005 | Chopra |
| 2005/0153885 A1 | 7/2005 | Yun et al. |
| 2005/0197679 A1 | 9/2005 | Dawson |
| 2005/0202398 A1 | 9/2005 | Hegemann et al. |
| 2005/0215764 A1 | 9/2005 | Tuszynski et al. |
| 2005/0240127 A1 | 10/2005 | Seip et al. |
| 2005/0267011 A1 | 12/2005 | Deisseroth et al. |
| 2005/0267454 A1 | 12/2005 | Hissong et al. |
| 2006/0025756 A1 | 2/2006 | Francischelli et al. |
| 2006/0034943 A1 | 2/2006 | Tuszynski |
| 2006/0057192 A1 | 3/2006 | Kane |
| 2006/0058671 A1 | 3/2006 | Vitek et al. |
| 2006/0058678 A1 | 3/2006 | Vitek et al. |
| 2006/0100679 A1 | 5/2006 | DiMauro et al. |
| 2006/0106543 A1 | 5/2006 | Deco et al. |
| 2006/0155348 A1 | 7/2006 | deCharms |
| 2006/0161227 A1 | 7/2006 | Walsh et al. |
| 2006/0184069 A1 | 8/2006 | Vaitekunas |
| 2006/0190044 A1 | 8/2006 | Libbus et al. |
| 2006/0206172 A1 | 9/2006 | DiMauro et al. |
| 2006/0216689 A1 | 9/2006 | Maher et al. |
| 2006/0236525 A1 | 10/2006 | Sliwa et al. |
| 2006/0241697 A1 | 10/2006 | Libbus et al. |
| 2006/0253177 A1 | 11/2006 | Taboada et al. |
| 2006/0271024 A1 | 11/2006 | Gertner et al. |
| 2007/0031924 A1 | 2/2007 | Li et al. |
| 2007/0053996 A1 | 3/2007 | Boyden et al. |
| 2007/0054319 A1 | 3/2007 | Deisseroth et al. |
| 2007/0060915 A1 | 3/2007 | Kucklick |
| 2007/0135875 A1 | 6/2007 | Demarais et al. |
| 2007/0156180 A1 | 7/2007 | Jaax et al. |
| 2007/0196838 A1 | 8/2007 | Chesnut et al. |
| 2007/0197918 A1 | 8/2007 | Vitek et al. |
| 2007/0219600 A1 | 9/2007 | Gertner et al. |
| 2007/0220628 A1 | 9/2007 | Glassman et al. |
| 2007/0239080 A1 | 10/2007 | Schaden et al. |
| 2007/0239210 A1 | 10/2007 | Libbus et al. |
| 2007/0253995 A1 | 11/2007 | Hildebrand et al. |
| 2007/0261127 A1 | 11/2007 | Boyden et al. |
| 2007/0282404 A1 | 12/2007 | Cottrell et al. |
| 2007/0295978 A1 | 12/2007 | Coushaine et al. |
| 2008/0020465 A1 | 1/2008 | Padidam |
| 2008/0027505 A1 | 1/2008 | Levin et al. |
| 2008/0033569 A1 | 2/2008 | Ferren et al. |
| 2008/0046053 A1 | 2/2008 | Wagner et al. |
| 2008/0050770 A1 | 2/2008 | Zhang et al. |
| 2008/0051673 A1 | 2/2008 | Kong et al. |
| 2008/0060088 A1 | 3/2008 | Shin et al. |
| 2008/0065158 A1 | 3/2008 | Ben-Ezra et al. |
| 2008/0065183 A1 | 3/2008 | Whitehurst et al. |
| 2008/0077200 A1 | 3/2008 | Bendett et al. |
| 2008/0085265 A1 | 4/2008 | Schneider et al. |
| 2008/0103551 A1 | 5/2008 | Masoud |
| 2008/0119421 A1 | 5/2008 | Tuszynski et al. |
| 2008/0125836 A1 | 5/2008 | Streeter et al. |
| 2008/0167261 A1 | 7/2008 | Sclimenti |
| 2008/0175819 A1 | 7/2008 | Kingsman et al. |
| 2008/0200749 A1 | 8/2008 | Zheng et al. |
| 2008/0221452 A1 | 9/2008 | Njemanze |
| 2008/0227139 A1 | 9/2008 | Deisseroth et al. |
| 2008/0228244 A1 | 9/2008 | Pakhomov et al. |
| 2008/0262411 A1 | 10/2008 | Dobak |
| 2008/0287821 A1 | 11/2008 | Jung et al. |
| 2009/0054954 A1 | 2/2009 | Foley et al. |
| 2009/0069261 A1 | 3/2009 | Dodge et al. |
| 2009/0088680 A1 | 4/2009 | Aravanis et al. |
| 2009/0093403 A1 | 4/2009 | Zhang et al. |
| 2009/0099038 A1 | 4/2009 | Deisseroth et al. |
| 2009/0112133 A1 | 4/2009 | Deisseroth et al. |
| 2009/0118800 A1 | 5/2009 | Deisseroth et al. |
| 2009/0148861 A1 | 6/2009 | Pegan et al. |
| 2009/0254134 A1 | 10/2009 | Nikolov et al. |
| 2009/0268511 A1 | 10/2009 | Birge et al. |
| 2009/0319008 A1 | 12/2009 | Mayer |
| 2009/0326603 A1 | 12/2009 | Boggs |
| 2010/0009444 A1 | 1/2010 | Herlitze et al. |
| 2010/0016783 A1 | 1/2010 | Bourke et al. |
| 2010/0145418 A1 | 6/2010 | Zhang et al. |
| 2010/0190229 A1 | 7/2010 | Zhang et al. |
| 2010/0234273 A1 | 9/2010 | Boyden et al. |
| 2011/0092800 A1 | 4/2011 | Yoo et al. |
| 2011/0105998 A1 | 5/2011 | Zhang et al. |
| 2011/0112179 A1 | 5/2011 | Deisseroth et al. |
| 2011/0125077 A1 | 5/2011 | Denison et al. |
| 2011/0125078 A1 | 5/2011 | Denison et al. |
| 2011/0159562 A1 | 6/2011 | Deisseroth et al. |
| 2011/0166632 A1 | 7/2011 | Deisseroth et al. |
| 2011/0172653 A1 | 7/2011 | Deisseroth et al. |
| 2011/0301529 A1 | 12/2011 | Zhang et al. |
| 2011/0311489 A1 | 12/2011 | Deisseroth et al. |
| 2012/0093772 A1 | 4/2012 | Horsager et al. |

(56) References Cited

U.S. PATENT DOCUMENTS

| | | |
|---|---|---|
| 2012/0253261 A1 | 10/2012 | Poletto et al. |
| 2013/0144359 A1 | 6/2013 | Kishawi et al. |

FOREIGN PATENT DOCUMENTS

| | | |
|---|---|---|
| WO | WO 2009-131837 | 10/2009 |
| WO | WO 2010/011404 A3 | 1/2010 |
| WO | WO 2010/056970 | 5/2010 |
| WO | WO 2011/066320 A3 | 6/2011 |
| WO | WO 2011-116238 A2 | 9/2011 |
| WO | WO 2011/127088 A3 | 10/2011 |
| WO | WO 2012/061676 | 5/2012 |
| WO | WO2012/061681 | 5/2012 |
| WO | WO2012/061684 | 5/2012 |
| WO | WO2012/061688 | 5/2012 |
| WO | WO2012/061690 | 5/2012 |
| WO | WO 2012/061744 | 5/2012 |
| WO | WO 2012/134704 A2 | 10/2012 |
| WO | WO 2013/126521 | 8/2013 |
| WO | WO 2013/142196 | 9/2013 |

OTHER PUBLICATIONS

Aebischer, et al. "Long-Term Cross-Species Brain Transplantation of a Polymer-Encapsulated Dopamine-Secreting Cell Line", Experimental Neurology, 1991, vol. 111, pp. 269-275.
Ahmad, et al. "The *Drosophila* rhodopsin cytoplasmic tail domain is required for maintenance of rhabdomere structure." The FASEB Journal, 2007, vol. 21, p. 449-455.
Akirav, et al. "The role of the medial prefrontal cortex-amygdala circuit in stress effects on the extinction of fear", Neural Plasticity, 2007: vol. 2007 Article ID:30873, pp. 1-11.
Ang, et at. "Hippocampal CA1 Circuitry Dynamically Gates Direct Cortical Inputs Preferentially at Theta Frequencies." The Journal of Neurosurgery, 2005, vol. 25, No. 42, pp. 9567-9580.
Araki, et al. "Site-Directed Integration of the *cre* Gene Mediated by Cre Recombinase Using a Combination of Mutant *lox* Sites", Nucleic Acids Research, 2002, vol. 30, No. 19, pp. 1-8.
Aravanis, et al. "An optical neural interface: in vivo control of rodent motor cortex with integrated fiberoptic and optogenetic technology," J. Neural. Eng., 2007, vol. 4(3):S143-S156.
Argos, et al. "The integrase family of site-specific recombinases: regional similarities and global diversity", The EMBO Journal, 1986, vol. 5, No. 2, pp. 433-440.
Bamberg et al. "Light-driven proton or chloride pumping by halorhodopsin." Proc. Natl. Academy Science USA, 1993, vol. 90, No. 2, p. 639-643.
Banghart, et al. "Light-activated ion channels for remote control of neuronal firing". Nature Neuroscience, 2004, vol. 7, No. 12 pp. 1381-1386.
Basil et al. "Is There Evidence for Effectiveness of Transcranial Magnetic Stimulation in the Treatment of Psychiatric Disorders?" Psychiatry, 2005, pp. 64-69.
Bebbington et al., The use of vectors based on gene amplification for the expression of cloned genes in mammalian cells in "DNA cloning" vol. 3, Academic Press, New York, 1987.
Benabid "Future strategies to restore brain functions," Conference proceedings from Medicine Meets Millennium: World Congress of Medicine and Health, 2000, 6 pages.
Benoist et al. "In vivo sequence requirements of the SV40 early promotor region" Nature (London), 1981, vol. 290(5804): pp. 304-310.
Berges et al., "Transduction of Brain by Herpes Simplex Virus Vectors", Molecular Therapy, 2007, vol. 15, No. 1: pp. 20-29.
Berridge et al., "The Versatility and Universality of Calcium Signaling", Nature Reviews: Molecular Cell Biology, 2000, vol. 1: pp. 11-21.
Bocquet et al. "A prokaryotic proton-gated ion channel from the nicotinic acetylcholine receptor family." Nature Letters, 2007, vol. 445, p. 116-119.
Boyden, et al. "Millisecond-timescale, genetically targeted optical control of neural activity" Nature Neuroscience, 2005, vol. 8, No. 9: pp. 1263-1268.
Bi, et al. "Ectopic Expression of a Microbial-Type Rhodopsin Restores Visual Responses in Mice with Photoreceptor Degeneration", Neuron, 2006, vol. 50, No. 1: pp. 23-33.
Bi, et al. "Synaptic Modifications in Cultured Hippocampal Neurons: Dependence on Spike Timing, Synaptic Strength, and Postsynaptic Cell Type", Journal of Neuroscience, 1998, vol. 18, No. 24: pp. 10464-1 0472.
Blomer et al., "Highly Efficient and Sustained Gene Transfer in Adult Neurons with Lentivirus Vector", Journal of Virology,1997, vol. 71, No. 9: pp. 6641-6649.
Brinton, et al. "Preclinical analyses of the therapeutic potential of allopregnanolone to promote neurogenesis in vitro and in vivo in transgenic mouse model of Alzheimer's disease." Current Alzheimer Research, 2006, vol. 3, No. 1: pp. 11-17.
Brosenitsch et al, "Physiological Patterns of Electrical Stimulation Can Induce Neuronal Gene Expression by Activating N-Type Calcium Channels," Journal of Neuroscience, 2001, vol. 21, No. 8, pp. 2571-2579.
Brown, et al. "Long-term potentiation induced by θ frequency stimulation is regulated by a protein phosphate-operated gate." The Journal of Neuroscience, 2000, vol. 20, No. 21, pp. 7880-7887.
Callaway, et al. "Photostimulation using caged glutamate reveals functional circuitry in living brain slices", Proc. Natl. Acad. Sci. USA., 1993, vol. 90: pp. 7661-7665.
Campagnola et al. "Fiber-coupled light-emitting diode for localized photostimulation of neurons expressing channelrhodopsin-2." Journal of Neuroscience Methods , 2008, vol. 169, Issue 1. Abstract only.
Cenatiempo "Prokaryotic gene expression in vitro: transcription-translation coupled systems", Biochimie, 1986, vol. 68(4): pp. 505-515.
Claudio et al. "Nucleotide and deduced amino acid sequences of *Torpedo californica* acetylcholine receptor gamma subunit." PNAS USA,1983, vol. 80, p. 1111-1115.
Collingridge et al. "Inhibitory post-synaptic currents in rat hippocampal CA1 neurones." J. Physiol., 1984, vol. 356, pp. 551-564.
Covington, et al. "Antidepressant Effect of Optogenetic Stimulation of the Medial Prefrontal Cortex." Journal of Neuroscience, 2010, vol. 30(48), pp. 16082-16090.
Crouse, et al. "Expression and amplification of engineered mouse dihydrofolate reductase minigenes" Mol. Cell. Biol. , 1983, vol. 3(2): pp. 257-266.
Cucchiaro et al., "*Phaseolus vulgaris* leucoagglutinin (PHA-L): a neuroanatomical tracer for electron microscopic analysis of synaptic circuitry in the cat's dorsal lateral geniculate nucleus" J. Electron. Microsc. Tech., 1990, 15 (4):352-368.
Cucchiaro et al., "Electron-Microsoft Analysis of Synaptic Input from the Perigeniculate Nucleus to A-Lamine of the Lateral Geniculate Nucleus in Cats", The Journal of Comparitive Neurology, 1991, vol. 310, pp. 316-336.
Cui, et al., "Electrochemical deposition and characterization of conducting polymer polypyrrole/PSS on multichannel neural probes," Sensors and Actuators, 2001, vol. 93(1):pp. 8-18.
Date, et al. "Grafting of Encapsulated Dopamine-Secreting Cells in Parkinson's Disease: Long-Term Primate Study", Cell Transplant, 2000, vol. 9, pp. 705-709.
Dalva, et al. "Rearrangements of Synaptic Connections in Visual Cortex Revealed by Laser Photostimulation", Science, 1994,vol. 265, pp. 255-258.
Dederen, et al. "Retrograde neuronal tracing with cholera toxin B subunit: comparison of three different visualization methods", Histochemical Journal, 1994, vol. 26, pp. 856-862.
Deisseroth et al., "Signaling from Synapse to Nucleus: Postsynaptic CREB Phosphorylation During Multiple Forms of Hippocampal Synaptic Plasticity", Neuron, 1996, vol. 16, pp. 89-101.
Deisseroth et al., "Translocation of Calmodulin to the Nucleus Supports CREB Phosphorylation in Hippocampal Neurons", Nature, 1998, vol. 392, pp. 198-202.
Deisseroth et al., "Signaling from Synapse to Nucleus: the logic Behind the Mechanisms", Currrent Opinion in Neurobiology, 2003, vol. 13, pp. 354-365.

(56) References Cited

OTHER PUBLICATIONS

Deisseroth "Next-generation optical technologies for illuminating genetically targeted brain circuits," The Journal of Neuroscience, 2006, vol. 26, No. 41, pp. 10380-10386.
Denk, W., et al. "Anatomical and functional imaging of neurons using 2-photon laser scanning microscopy", Journal of Neuroscience Methods, 1994, vol. 54, pp. 151-162.
Ditterich, et al. "Microstimulation of visual cortex affects the speed of perceptual decisions", 2003, Nature Neuroscience, vol. 6, No. 8, pp. 891-898.
Dittgen, et al. "Lentivirus-based genetic manipulations of cortical neurons and their optical and electrophysiological monitoring in vivo", PNAS, 2004, vol. 101, No. 52, pp. 18206-18211.
Ensell, et al. "Silicon-based microelectrodes for neurophysiology, micromachined from silicon-on-insulator wafers," Med. Biol. Eng. Comput., 2000, vol. 38, pp. 175-179.
Eisen, "Treatment of amyotrophic lateral sclerosis", Drugs Aging, 1999; vol. 14, No. 3, pp. 173-196.
Evanko "Optical excitation yin and yang" Nature Methods, 2007, 4:384.
Esposito et al. "The integrase family of tyrosine recombinases: evolution of a conserved active site domain" , Nucleic Acids Research, 1997, vol. 25, No. 18, pp. 3605-3614.
Fabian et al. "Transneuronal transport of lectins" Brain Research, 1985, vol. 344, pp. 41-48.
Falconer et al. "High-throughput screening for ion channel modulators," Journal of Biomolecular Screening, 2002, vol. 7, No. 5, pp. 460-465.
Farber, et al. "Identification of Presynaptic Neurons by Laser Photostimulation", Science, 1983, vol. 222, pp. 1025-1027.
Feng, et al. "Imaging Neuronal Subsets in Transgenic Mice Expressing Multiple Spectral Variants of GFP", Neuron, 2000, vol. 28, pp. 41-51.
Fisher, J. et al. "Spatiotemporal Activity Patterns During Respiratory Rhythmogenesis in the Rat Ventrolateral Medulla," The Journal of Neurophysiol, 2006, vol. 95, pp. 1982-1991.
Fitzsimons et al., "Promotors and Regulatory Elements that Improve Adeno-Associated Virus Transgene Expression in the Brain", 2002, Methods, vol. 28, pp. 227-236.
Foster, "Bright blue times", Nature, 2005, vol. 433, pp. 698-699.
Gelvich et al. "Contact flexible microstrip applicators (CFMA) in a range from microwaves up to short waves," IEEE Transactions on Biomedical Engineering, 2002, vol. 49, Issue 9: 1015-1023.
Gigg, et al. "Glutamatergic hippocampal formation projections to prefrontal cortex in the rat are regulated by GABAergic inhibition and show convergence with glutamatergic projections from the limbic thalamus," Hippocampus, 1994, vol. 4, No. 2, pp. 189-198.
Gilman, et al. "Isolation of sigma-28-specific promoters from *Bacillus subtilis* DNA" Gene, 1984, vol. 32(1-2): pp. 11-20.
Glick et al."Factors affecting the expression of foreign proteins in *Escherichia coli*", Journal of Industrial Microbiology, 1987, vol. 1(5): pp. 277-282.
Goekoop, R. et al. "Cholinergic challenge in Alzheimer patients and mild cognitive impairment differentially affects hippocampal activation—a pharmacological fMRI study." Brain, 2006, vol. 129, pp. 141-157.
Gordon, et al. "Regulation of Thy-1 Gene Expression in Transgenic Mice", Cell, 1987, vol. 50, pp. 445-452.
Gorelova et al. , "The course of neural projection from the prefrontal cortex to the nucleus accumbens in the rat ", Neuroscience, 1997, vol. 76, No. 3, pp. 689-706.
Gottesman et al."Bacterial regulation: global regulatory networks," Ann. Rev. Genet. , 1984, vol. 18, pp. 415-441.
Greenberg, et al. "Three-year outcomes in deep brain stimulation for highly resistant obsessive-compulsive disorder," Neuropsychopharmacology, 2006, vol. 31, pp. 2384-2393.
Groth et al. "Phage integrases: biology and applications," Journal of Molecular Biology, 2004, vol. 335, pp. 667-678.
Groth, et al. "A phage integrase directs efficient site-specific integration in human cells", PNAS, 2000, vol. 97, No. 11, pp. 5995-6000.
Guatteo, et al. "Temperature sensitivity of dopaminergic neurons of the substantia nigra pars compacta: Involvement of transient receptor potential channels," Journal of Neurophysiol. , 2005, vol. 94, pp. 3069-3080.
Gur et al., "A Dissociation Between Brain Activity and Perception: Chromatically Opponent Cortical Neurons Signal Chromatic Flicker that is not Perceived", Vision Research, 1997, vol. 37, No. 4, pp. 377-382.
Hallet et al. "Transposition and site-specific recombination: adapting DNA cut-and-paste mechanisms to a variety of genetic rearrangements," FEMS Microbiology Reviews, 1997, vol. 21, No. 2, pp. 157-178.
Hamer, et al. "Regulation In Vivo of a cloned mammalian gene: cadmium induces the transcription of a mouse metallothionein gene in SV40 vectors," Journal of Molecular Applied Genetics, 1982, vol. 1, No. 4, pp. 273-288.
Hegemann et al., "All-trans Retinal Constitutes the Functional Chromophore in *Chlamydomonas* rhodopsin", Biophys. J. , 1991, vol. 60, pp. 1477-1489.
Herry, et al. "Switching on and off fear by distinct neuronal circuits," Nature, 2008, vol. 454, pp. 600-606.
Hildebrandt et al, "Bacteriorhodopsin expressed in *Schizosaccharomyces pombe* pumps protons through the plasma membrane, " PNAS, 1993, vol. 90, pp. 3578-3582.
Hirase, et al. "Multiphoton stimulation of neurons", J Neurobiol, 2002, vol. 51, No. 3: pp. 237-47.
Hodaie, et al., "Chronic Anterior Thalamus Stimulation for Intractable Epilepsy," Epilepsia, 2002, vol. 43, pp. 603-608.
Hoffman et al., "K+ Channel Regulation of Signal Propagation in Dendrites of Hippocampal Pyramidal Neurons", 1997, Nature, vol. 387: pp. 869-874.
Hosokawa, T. et al. "Imaging spatio-temporal patterns of long-term potentiation in mouse hippocampus." Philos. Trans. R. Soc. Lond. B., 2003, vol. 358, pp. 689-693.
Hynynen, et al. "Clinical applications of focused ultrasound—The brain." Int. J. Hyperthermia, 2007, vol. 23, No. 2: pp. 193-202.
International Search Report for International Application No. PCT/US2009/053474, dated Oct. 8, 2009.
Isenberg et al. "Cloning of a Putative Neuronal Nicotinic Aceylcholine Receptor Subunit," Journal of Neurochemistry, 1989, pp. 988-991.
Johnston et al. "Isolation of the yeast regulatory gene *GAL4* and analysis of its dosage effects on the galactose/melibiose regulon," PNAS, 1982, vol. 79, pp. 6971-6975.
Kandel, E.R.,et al. "Electrophysiology of Hippocampal Neurons: I. Sequential Invasion and Synaptic Organization," J Neurophysiol, 1961, vol. 24, pp. 225-242.
Kandel, E.R.,et al. "Electrophysiology of Hippocampal Neurons: II. After-Potentials and Repetitive Firing", J Neurophysiol., 1961, vol. 24, pp. 243-259.
Karreman et al. "On the use of double FLP recognition targets (FRTs) in the LTR of retroviruses for the construction of high producer cell lines" , Nucleic Acids Research, 1996, vol. 24, No. 9: pp. 1616-1624.
Kato et al. "Present and future status of noninvasive selective deep heating using RF in hyperthermia." Med & Biol. Eng. & Comput 31 Supp: S2-11, 1993. Abstract. p. S2 only.
Katz, et al. "Scanning laser photostimulation: a new approach for analyzing brain circuits," Journal of Neuroscience Methods, 1994, vol. 54, pp. 205-218.
Khodakaramian, et al. "Expression of Cre Recombinase during Transient Phage Infection Permits Efficient Marker Removal in *Streptomyces*," Nucleic Acids Research, 2006, vol. 34, No. 3:e20, pp. 1-5.
Khossravani et al., "Voltage-Gated Calcium Channels and Idiopathic Generalized Epilepsies", Physiol. Rev., 2006, vol. 86: pp. 941-966.
Kim et al., "Light-Driven Activation of β2-Adrenergic Receptor Signaling by a Chimeric Rhodopsin Containing the β2-Adrenergic Receptor Cytoplasmic Loops," Biochemistry, 2005, vol. 44, No. 7, pp. 2284-2292.
Kingston et al. "Transfection of DNA into Eukaryotic Cells," Supplement 63, Current Protocols in Molecular Biology, 1996, 9.1.1-9.1.11, 11 pages.

(56) References Cited

OTHER PUBLICATIONS

Kita, H. et al. "Effects of dopamine agonists and antagonists on optical responses evoked in rat frontal cortex slices after stimulation of the subcortical white matter," Exp. Brain Research, 1999, vol. 125, pp. 383-388.
Kitayama, et al. "Regulation of neuronal differentiation by N-methyl-D-aspartate receptors expressed in neural progenitor cells isolated from adult mouse hippocampus," Journal of Neurosci Research, 2004, vol. 76, No. 5: pp. 599-612.
Klausberger, et al. "Brain-state- and cell-type-specific firing of hippocampal interneurons in vivo", Nature, 2003, vol. 421: pp. 844-848.
Kocsis et al., "Regenerating Mammalian Nerve Fibres: Changes in Action Potential Wavefrom and Firing Characteristics Following Blockage of Potassium Conductance", 1982, Proc. R. Soc. Lond., vol. B 217: pp. 77-87.
Kuhlman et al. (2008) "High-Resolution Labeling and Functional Manipulation of Specific Neuron Types in Mouse Brain by Cre-Activated Viral Gene Expression" PLoS One, 2005, vol. 3, No. 4, pp. 1-11.
Kunkler, P. et at. "Optical Current Source Density Analysis in Hippocampal Organotypic Culture Shows that Spreading Depression Occurs with Uniquely Reversing Current," The Journal of Neuroscience, 2005, vol. 25, No. 15, pp. 3952-3961.
Landy, A. "Mechanistic and structural complexity in the site-specific recombination pathways of Int and FLP", Current Opinion in Genetics and Development, 1993, vol. 3, pp. 699-707.
Lee et al. "Sterotactic Injection of Adenoviral Vectors that Target Gene Expression to Specific Pituitary Cell Types: Implications for Gene Therapy", Neurosurgery, 2000, vol. 46, No. 6: pp. 1461-1469.
Lee et al., "Potassium Channel Gone Therapy Can Prevent Neuron Deatch Resulting from Necrotic and Apoptotic Insults", Journal of Neurochemistry, 2003, vol. 85: pp. 1079-1088.
Levitan et al. "Surface Expression of Kv1 Voltage-Gated K+ Channels Is Governed by a C-terminal Motif," Trends Cardiovasc. Med., 2000, vol. 10, No. 7, pp. 317-320.
Li et al. "Fast noninvasive activation and inhibition of neural and network activity by vertebrate rhodopsin and green algae channelrhodopsin." PNAS, 2005, vol. 102, No. 49, p. 17816-17821.
Lim et al., "A Novel Targeting Signal for Proximal Clustering of the Kv2.1K+ Channel in Hippocampal Neurons", Neuron, 2000, vol. 25: pp. 385-397.
Lima, et al. "Remote Control of Behavior through Genetically Targeted Photostimulation of Neurons", Cell, 2005, vol. 121: pp. 141-152.
Liman, et al. "Subunit Stoichiometry of a Mammalian K+ Channel Determined by Construction of Multimeric cDNAs," Neuron, 1992, vol. 9, pp. 861-871.
Luecke, et al. "Structural Changes in Bacteriorhodopsin During Ion Transport at 2 Angstrom Resolution," Science, 1999, vol. 286, pp. 255-260.
Lyznik, et al. "FLP-mediated recombination of FRT sites in the maize genome," Nucleic Acids Research , 1996, vol. 24, No. 19: pp. 3784-3789.
Ma et al. "Role of ER Export Signals in Controlling Surface Potassium Channel Numbers," Science, 2001, vol. 291, pp. 316-319.
Mann et at. "Perisomatic Feedback Inhibition Underlies Cholinergically Induced Fast Network Oscillations in the Rat Hippocampus in Vitro," Neuron, 2005, vol. 45, 2005, pp. 105-117.
Mattson, "Apoptosis in Neurodegenerative Disorders", Nature Reviews, 2000, vol. 1: pp. 120-129.
Mayberg et al. "Deep Brain Stimulation for Treatment-Resistant Depression," Focus, 2008, vol. VI, No. 1, pp. 143-154.
McKnight "Functional relationships between transcriptional control signals of the thymidine kinase gene of herpes simplex virus", Cell, 1982, vol. 31 pp. 355-365.
Melyan, Z., et al. "Addition of human melanopsin renders mammalian cells Photoresponsive", Nature, 2005, vol. 433: pp. 741-745.
Mermelstein, et al. "Critical Dependence of cAMP Response Element-Binding Protein Phosphorylation on L-Type Calcium Channels Supports a Selective Response to EPSPs in Preference to Action Potentials", The Journal of Neuroscience, 2000, vol. 20, No. 1, pp. 266-273.
Meyer, et al. "High density interconnects and flexible hybrid assemblies for active biomedical implants," IEEE Transactions on Advanced Packaging , 2001, vol. 24, No. 3, pp. 366-372.
Monje et al., "Irradiation Induces Neural Precursor-Cell Dysfunction", Natural Medicine, 2002, vol. 8, No. 9, pp. 955-962.
Nacher, et al. "NMDA receptor antagonist treatment increases the production of newneurons in the aged rat hippocampus", Neurobiology of Aging, 2003, vol. 24, No. 2: pp. 273-284.
Nagel et al."Functional Expression of Bacteriorhodopsin in Oocytes Allows Direct Measurement of Voltage Dependence of Light Induced H+ Pumping," FEBS Letters, 1995, vol. 377, pp. 263-266.
Nagel, et al. "Channelrhodopsin-I: a light-gated proton channel in green algae", Science, 2002, vol. 296: pp. 2395-2398.
Nagel, et al. "Channelrhodopsin-2, a directly light-gated cation-selective membrane channel", PNAS, 2003, vol. 100, No. 24: pp. 13940-13945.
Nakagami, et al. "Optical Recording of Trisynaptic Pathway in Rat Hippocampal Slices with a Voltage-Sensitive Dye" Neuroscience, 1997, vol. 81, No. 1, pp. 1-8.
Naqvi, et al. "Damage to the insula disrupts addiction to cigarette smoking," Science; 2007, vol. 315 pp. 531-534.
Nirenberg, et al. "The Light Response of Retinal Ganglion Cells is Truncated by a Displaced Amacrine Circuit", Neuron, 1997, vol. 18: pp. 637-650.
Nunes-Duby, et al. "Similarities and differences among 105 members of the Int family of site-specific recombinases" , Nucleic Acids Research, 1998, vol. 26, No. 2: pp. 391-406.
O'Gorman et al. "Recombinase-mediated gene activation and site-specific integration in mammalian cells", Science, 1991, 251(4999): pp. 1351-1355.
Olivares (2001) "Phage R4 integrase mediates site-specific integration in human cells", Gene, 2001, vol. 278, pp. 167-176.
Ory, et al. "A stable human-derived packaging cell line for production of high titer retrovirus/vesicular stomatitis virus G pseudotypes," PNAS, 1996, vol. 93: pp. 11400-11406.
Palmer et al., "The Adult Rat Hippocampus Contains Primordial Neural Stem Cells", Molecular and Cellular Neuroscience, 1997, vol. 8, pp. 389-404.
Palmer et al., "Fibroblast Growth Factor-2 Activates a Latent Neurogenic Program in Neural Stem Cells from Diverse Regions of the Adult CNS", The Journal of Neuroscience, 1999, vol. 19, pp. 8487-8497.
Pan et al. "Functional Expression of a Directly Light-Gated Membrane Channel in Mammalian Retinal Neurons: A Potential Strategy for Restoring Light Sensitivity to the Retina After Photoreceptor Degeneration,"Investigative Opthalmology & Visual Science, 2005, 46 E-Abstract 4631. Abstract only.
Panda, et al. " Illumination of the Melanopsin Signaling Pathway", Science, 2005, vol. 307: pp. 600-604.
Paulhe et al. "Specific Endoplasmic Reticulum Export Signal Drives Transport of Stem Cell Factor (Kitl) to the Cell Surface," The Journal of Biological Chemistry, 2004, vol. 279, No. 53, p. 55545-55555.
Pear "Transient Transfection Methods for Preparation of High-Titer Retroviral Supernatants" Supplement 68, Current Protocols in Molecular Biology, 1996, 9.1 1 .1 -9.1 1 .1 8.
Petersen et al. "Spatiotemporal Dynamics of Sensory Responses in Layer 2/3 of Rat Barrel Cortex Measured In Vivo by Voltage-Sensitive Dye Imaging Combined with Whole-Cell Voltage Recordings and Neuron Reconstructions," The Journal of Neuroscience, 2003, vol. 23, No. 3, pp. 1298-1309.
Petrecca, et al. "Localization and Enhanced Current Density of the Kv4.2 Potassium Channel by Interaction with the Actin-Binding Protein Filamin," The Journal of Neuroscience, 2000, vol. 20, No. 23, pp. 8736-8744.
Pettit, et al. "Local Excitatory Circuits in the Intermediate Gray Layer of the Superior Colliculus", J Neurophysiol., 1999, vol. 81, No. 3: pp. 1424-1427.

(56) References Cited

OTHER PUBLICATIONS

Potter, "Transfection by Electroporation." Supplement 62, Current Protocols in Molecular Biology, 1996, 9.3.1-9.3.6.
Qiu et al. "Induction of photosensitivity by heterologous expression of melanopsin", Nature, 2005, vol. 433: pp. 745-749.
Rathnasingham et al., "Characterization of implantable microfabricated fluid delivery devices," IEEE Transactions on Biomedical Engineering, 2004, vol. 51, No. 1: pp. 138-145.
Rivera et al., "BDNF-Induced TrkB Activation Down-Regulates the K+-Cl-cotransporter KCC2 and Impairs Neuronal Cl-Extrusion", The Journal of Cell Biology, 2002, vol. 159: pp. 747-752.
Rosenkranz, et al. "The prefrontal cortex regulates lateral amygdala neuronal plasticity and responses to previously conditioned stimuli", J. Neurosci., 2003, vol. 23, No. 35: pp. 11054-11064.
Rousche, et al., "Flexible polyimide-based intracortical electrode arrays with bioactive capability," IEEE Transactions on Biomedical Engineering, 2001, vol. 48, No. 3, pp. 361-371.
Rubinson et at. "A lentivirus-based system to functionally silence genes in primary mammalian cells, stem cells and transgenic mice by RNA interference," Nature Genetics, 2003, vol. 33, p. 401-406.
Rudiger et at. "Specific arginine and threonine residues control anion binding and transport in the light-driven chloride pump halorhodopsin," The EMBO Journal, 1997, vol. 16, No. 13, pp. 3813-3821.
Salzman, et al. "Cortical microstimulation influences perceptual judgements of motion direction", Nature, 1990, vol. 346, pp. 174-177.
Sato et al. "Role of Anion-binding Sites in cytoplasmic and extracellular channels of *Natronomonas pharaonis* halorhodopsin," Biochemistry, 2005. vol. 44, pp. 4775-4784.
Sauer "Site-specific recombination: developments and applications," Current Opinion in Biotechnology, 1994, vol. 5, No. 5: pp. 521-527.
Schiff, et al. "Behavioral improvements with thalamic stimulation after severe traumatic brain injury," Nature, 2007, vol. 448, pp. 600-604.
Schlaepfer et al. "Deep Brain stimulation to Reward Circuitry Alleviates Anhedonia in Refractory Major Depression," Neuropsychopharmacology, 2008,vol. 33, pp. 368-377.
Sclimenti, et al. "Directed evolution of a recombinase for improved genomic integration at a native human sequence," Nucleic Acids Research, 2001, vol. 29, No. 24: pp. 5044-5051.
Shepherd, et al. "Circuit Analysis of Experience-Dependent Plasticity in the Developing Rat Barrel Cortex", Neuron, 2003, vol. 38: pp. 277-289.
Shibasaki et al. "Effects of body temperature on neural activity in the hippocampus: Regulation of resting membrane potentials by transient receptor potential vanilloid 4," The Journal of Neuroscience, 2007, vol. 27, No. 7: pp. 1566-1575.
Silver, et al. "Amino terminus of the yeast *GAL4* gene product is sufficient for nuclear localization" PNAS, 1984, vol. 81, No. 19: pp. 5951-5955.
Singer et al. "Elevated Intrasynaptic Dopamine Release in Tourette's Syndrome Measured by PET," American Journal of Psychiatry, 2002, vol. 159: pp. 1329-1336.
Slimko et al., "Selective Electrical Silencing of Mammalian Neurons In Vitro by the use of Invertebrate Ligand-Gated Chloride Channels", The Journal of Neuroscience, 2002, vol. 22, No. 17: pp. 7373-7379.
Smith et al. "Diversity in the serine recombinases", Molecular Microbiology, 2002, vol. 44, No. 2: pp. 299-307.
Stark, et al. "Catalysis by site-specific recombinases," Trends Genet., 1992, vol. 8, No. 12: pp. 432-439.
Stockklausner et al. "A sequence motif responsible for ER export and surface expression of Kir2.0 inward rectifier K+ channels," FEBS Letters, 2001, vol. 493, pp. 129-133.
Stoll, et al. "Phage TP901-I site-specific integrase functions in human cells," Journal of Bacteriology, 2002, vol. 184, No. 13: pp. 3657-3663.
Takahashi, et al."Diversion of the Sign of Phototaxis in a *Chlamydomonas reinhardtii* Mutant Incorporated with Retinal and Its Analogs," FEBS Letters, 1992, vol. 314, No. 3, pp. 275-279.
Tatarkiewicz, et al. "Reversal of Hyperglycemia in Mice After Subcutaneous Transplantation of Macroencapsulated Islets", Transplantation, 1999, vol. 67, No. 5: pp. 665-671.
Tottene et al., "Familial Hemiplegic Migraine Mutations Increase $Ca^{2+}$ Influx Through Single Human $Ca_v2.1$ Current Density in Neurons", PNAS USA, 2002, vol. 99, No. 20: pp. 13284-13289.
Tsau et al. "Distributed Aspects of the Response to Siphon Touch in *Aplysia*: Spread of Stimulus Information and Cross-Correlation Analysis," The Journal of Neuroscience, 1994, vol. 14, No. 7, pp. 4167-4184.
[No Authors Listed] "Two bright new faces in gene therapy," Nature Biotechnology, 1996, vol. 14: p. 556.
Tye et. al., "Amygdala circuitry mediating reversible and bidirectional control of anxiety", Nature, 2011, vol. 471(7338): pp. 358-362.
Tye et. al., Supplementary Materials: "An optically-resolved microcircuit for bidirectional anxiety control", Nature, 2011, vol. 471(7338): pp. 358-362.
Ulmanen, et al. "Transcription and translation of foreign genes in *Bacillus subtilis* by the aid of a secretion vector," Journal of Bacteriology, 1985, vol. 162, No. 1: pp. 176-182.
Van Der Linden, "Functional brain imaging and pharmacotherapy in social phobia: single photon emission computed tomography before and after Treatment with the selective serotonin reuptake inhibitor citalopram," Prog Neuro-psychopharmacol Biol Psychiatry, 2000, vol. 24, No. 3: pp. 419-438.
Vanin, et al. "Development of high-titer retroviral producer cell lines by using Cre-mediated recombination," Journal of Virology, 1997, vol. 71, No. 10: pp. 7820-7826.
Vetter, et al. "Development of a Microscale Implantable Neural Interface (MINI) Probe System," Proceedings of the 2005 IEEE, Engineering in Medicine and Biology 27th Annual Conference, Shanghai, China, Sep. 1-4, 2005.
Wagner, "Noninvasive Human Brain Stimulation", Annual Rev. Biomed. Eng. 2007. 9:19.1-19.39.
Ward, et al. "Construction and characterisation of a series of multicopy promoter-probe plasmid vectors for *Streptomyces* using the aminoglycoside phosphotransferase gene from Tn5 as indicator", 1986, Mol. Gen. Genet., vol. 203: pp. 468-478.
Watson, et al. "Targeted transduction patterns in the mouse brain by lentivirus vectors pseudotyped with VSV, Ebola, Mokola, LCMV, or MuLV envelope proteins," Molecular Therapy, 2002, vol. 5, No. 5, pp. 528-537.
Wang et al. "Direct-current Nanogenerator Driven by Ultrasonic Waves," Science, 2007, vol. 316, pp. 102-105.
Wang et. al., "High-speed mapping of synaptic connectivity using photostimulation in Channelrhodopsin-2 transgenic mice", PNAS, 2007, vol. 104, No. 19, pp. 8143-8148.
Weick et al. "Interactions with PDZ Proteins Are Required for L-Type Calcium Channels to Activate cAMP Response Element-Binding Protein-Dependent Gene Expression," The Journal of Neuroscience, 2003, vol. 23, No. 8, pp. 3446-3456.
Witten et. al., Supporting Online Material for: "Cholinergic Interneurons Control Local Circuit Activity and Cocaine Conditioning", Science, 2010, vol. 330: 17 pages.
Witten et. al., "Cholinergic Interneurons Control Local Circuit Activity and Cocaine Conditioning", Science, 2010, vol. 330, No. 6011: pp. 1677-1681.
Yamazoe, et al. "Efficient generation of dopaminergic neurons from mouse embryonic stem cells enclosed in hollow fibers", Biomaterials, 2006, vol. 27, pp. 4871-4880.
Yan et al., "Cloning and Characterization of a Human β,β-Carotene-15, 15'-Dioxygenase that is Highly Expressed in the Retinal Pigment Epithelium", Genomics, 2001, vol. 72: pp. 193-202.
Yizhar et. al., "Neocortical excitation/inhibition balance in information processing and social dysfunction", Nature, 2011, vol. 477, pp. 171-178; and Supplemental Materials; 41 pages.
Yoon, et al., "A micromachined silicon depth probe for multichannel neural recording," IEEE Transactions Biomedical Engineering, 2000, vol. 47, No. 8, pp. 1082-1087.
Yoshimura, et al. "Excitatory cortical neurons form fine-scale functional networks", Nature, 2005, vol. 433: pp. 868-873.

(56) References Cited

OTHER PUBLICATIONS

Zacharias et al. "Recent advances in technology for measuring and manipulating cell signals," Current Opinion in Neurobiology, 2000, vol. 10: pp. 416-421.
Zemelman, et al. "Selective Photostimulation of Genetically ChARGed Neurons", Neuron, 2002, vol. 33: pp. 15-22.
Zemelman, et al. "Photochemical gating of heterologous ion channels: Remote control over genetically designated populations of neurons", PNAS, 2003, vol. 100, No. 3: pp. 1352-1357.
Zhang, et al. "Channelrhodopsin-2 and optical control of excitable cells," Nature Methods, 2006, vol. 3, No. 10, pp. 785-792.
Zhang, et al. "Red-Shifted Optogenetic Excitation: a Tool for Fast Neural Control Derived from *Volvox carteri*", Nature Neurosciences, 2008, vol. 11, No. 6, pp. 631-633.
Zhang "Multimodal fast optical interrogation of neural circuitry," Nature, 2007, vol. 446, pp. 633-641.
Zrenner, E., "Will Retinal Implants Restore Vision?" Science, 2002, vol. 295, No. 5557, pp. 1022-1025.
Zufferey, et al. "Self-Inactivating Lentivirus Vector for Safe and Efficient In Vivo Gene Delivery", Journal of Virology, 1998, vol. 72, No. 12, pp. 9873-9880.
Airan, et al., "Temporally Precise in vivo Control of Intracellular Signaling", 2009, Nature, vol. 458, No. 7241, pp. 1025-1029.
Braun, "Two Light-activated Conductances in the Eye of the Green Alga *Volvox carteri*", 1999, Biophys J., vol. 76, No. 3, pp. 1668-1678.
Cardin, et al. "Driving Fast spiking Cells Induces Gamma Rhythm and Controls Sensory Responses", 2009, Nature, vol. 459, vol. 7247, pp. 663-667.
Deisseroth et al., "Excitation-neurogenesis Coupling in Adult Neural Stem/Progenitor Cells", 2004, Neuron, vol. 42, pp. 535-552.
Ernst, et al. "Photoactivation of Channelrhodopsin", 2008, vol. 283, No. 3, pp. 1637-1643.
Genbank Accession No. DQ094781 (Jan. 15, 2008).
Gradinaru, et al. "ENpHR: a *Natronomonas* Halorhodopsin Enhanced for Optogenetic Applications", 2008, Brain Cell Biol., vol. 36 (1-4), pp. 129-139.
Herlitze, et al., "New Optical Tools for Controlling Neuronal Activity", 2007, Curr Opin Neurobiol, vol. 17, No. 1, pp. 87-94.
Jekely, "Evolution of Phototaxis", 2009, Phil. Trans. R. Soc. B, vol. 364, pp. 2795-2808.
Johansen, et al., "Optical Activation of Lateral Amygdala Pyramidal Cells Instructs Associative Fear Learning", 2010, PNAS, vol. 107, No. 28, pp. 12692-12697.
Kianianmomeni, et al. "Channelrhodopsins of *Volvox carteri* are Photochromic Proteins that are Specifically Expressed in Somatic Cells under Control of Light, Temperature, and the Sex Inducer", 2009, Plant Physiology, vol. 151, No. 1, pp. 347-366.
Knopfel, et al. "Optical Probin of Neuronal Circuit Dynamics: Gentically Encoded Versus Classical Fluorescent Sensors", 2006, Trends Neurosci, vol. 29, No. 3, pp. 160-166.
McAllister, "Cellular and Molecular Mechanisms of Dendrite Growth", 2000, Cereb Cortex, vol. 10, No. 10, pp. 963-973.
Pape, et al., "Plastic Synaptic Networks of the Amygdala for the Acquisition, Expression, and Extinction of Conditioned Fear", 2010, Physiol Rev, vol. 90, pp. 419-463.
Randic, et al. "Long-term Potentiation and Long-term Depression of Primary Afferent Neurotransmission in the Rat Spinal Cord", 1993, Journal of Neuroscience, vol. 13, No. 12, pp. 5228-5241.
Ritter, et al., "Monitoring Light-induced Structural Changes of Channelrhodopsin-2 by UV-Visable and Fourier Transform Infared Spectroscopy", 2008, The Journal of Biological Chemistry, vol. 283, No. 50, pp. 35033-35041.
Sajdyk, et al., "Excitatory Amino Acid Receptors in the Basolateral Amygdala Regulate Anxiety Responses in the Social Interaction Test", Brain Research, 1997, vol. 764, pp. 262-264.
Swanson, "Lights, Opsins, Action! Optogenetics Brings Complex Neuronal Circuits into Sharper Focus", 2009, The Dana Foundation, [URL: http://www.dana.org/news/features/detail.aspx?id=24236], PDF File, pp. 1-3.

Swiss-Prot_Q2QCJ4, Opsin 1, Oct. 31, 2006, URL: http://www.ncbi.nlm.nig.gov/protein/Q2QCJ4.
"SubName: Full=Channelrhodopsin-1", retrieved from EBI accession No. UNIPROT: B4Y103. Database accession No. B4Y103. Sep. 23, 2008.
U.S. Appl. No. 13/299,727, filed Nov. 18, 2011, Lee, et al.
Tam, B. et al., "Identification of an Outer Segment Targeting Signal in the COOH Terminus of Rhodopsin Using Transgenic *Xenopus laevis*", The Journal of Cell Biology, 2000, vol. 151, No. 7, pp. 1369-1380.
Lanyi et al. "The primary structure of a Halorhodopsin from *Natronobacterium pharaonis*; " Journal of Biological Chemistry 1990, vol. 265, No. 3, p. 1253-1260.
Hofherr et al. "Selective Golgi export of Kir2.1 controls the stoichiometry of functional Kir2.x channel heteromers"Journal of Cell Science, 2005, vol. 118, p. 1935-1943.
Loetterle, et al., "Cerebellar Stimulation: Pacing the Brain", American Journal of Nursing, 1975, vol. 75, No. 6, pp. 958-960.
Takahashi, et al., "Induction of Pluripotent Stem Cells from Mouse Embryonic and Adult Fibroblast Cultures by Defined Factors", 2006, Cell, vol. 126, pp. 663-676.
Adamantidis, et al., "Optogenetic Interrogation of Dopaminergic Modulation of the Multiple Phases of Reward-Seeking Behavior", J. Neurosci, 2011, vol. 31, No. 30, pp. 10829-10835.
Han, et al., "Multiple-Color Optical Activation, Silencing, and Desynchronization of Neural Activity with Single-Spike Temporal Resolution", PLoS One, 2007, vol. 2, No. 3, pp. 1-12.
Kinoshita, et al., "Optogenetically Induced Supression of Neural Activity in the Macaque Motor Cortex", Poster Sessions Somatomotor System, Others,2010, pp. 141-154.
Rein, et al., "The Optogenetic (r)evolution", Mol. Genet. Genomics, 2012, vol. 287, No. 2, pp. 95-109.
Remy, et al., "Depression in Parkinson's Disease: Loss of Dopamine and Noradrenaline Innervation in the Limbic System", Brain, 2005, vol. 128 (Pt 6), pp. 1314-1322.
Tsai, et al., "Phasic Firing in Dopaminergic Neurons in Sufficient for Behavioral Conditioning", Science, 2009, vol. 324, pp. 1080-1084.
Zhao, et al., "Improved Expression of Halorhodopsin for Light-Induced Silencing of Neuronal Activity", Brain Cell Biology, 2008, vol. 36 (1-4), pp. 141-154.
Balint, et al., "The Nitrate Transporting Photochemical Reaction Cycle of the Pharaonis Halorhodopsin", Biophysical Journal, 2004, vol. 86, pp. 1655-1663.
Gradinaru, et al., Molecular and Cellular Approaches for Diversifying and Extending Optogenetics, Cell, 2010, vol. 141, No. 1, pp. 154-165.
RecName: Full=Halorhodopsin; Short=HR; Alt Name: Full=NpHR; XP002704922, retrieved from EBI accession No. UNIPROT: P15647. Database accession No. P15647. Apr. 1, 1990.
"*N. pharaonis* halorhodopsin (hop) gene, complete cds.", XP002704883, retrieved from EBI accession No. EMBL: J05199. Database accession No. J05199. Nov. 22, 1990.
"Subname: Fluu= Bacteriorhodopsin"; XP002704863, retrieved from EBI accession No. UNIPROT: B0R5N9. Database accession No. B0R5N9. Apr. 8, 2008.
Zhang, et al., "The Microbial Opsin Family of Optogenetic Tools", Cell, 2011, vol. 147, No. 7, pp. 1146-1457.
Wang, et al., "Molecular Determinants Differentiating Photocurrent Properties of Two Channelrhodopsins from *Chlamydomonas*", 2009, The Journal of Biological Chemistry, vol. 284, No. 9, pp. 5685-5696.
Tye, et al. "Optogenetic investigation of neural circuits underlying brain disease in animal models," Nature Reviews Neuroscience (Mar. 2012), 13(4):251-266.
De Foubert et al. "Fluoxetine-Induced Change in Rat Brain Expression of Brain-Derived Neurotrophic Factor Varies Depending on Length of Treatment," Neuroscience, 2004, vol. 128, pp. 597-604.
Emerich, et al. "A Novel Approach to Neural Transplantation in Parkinson's Disease: Use of Polymer-Encapsulated Cell Therapy", Neuroscience and Biobehavioral Reviews, 1992, vol. 16, pp. 437-447.

(56) References Cited

OTHER PUBLICATIONS

Gold, et al. "Representation of a perceptual decision in developing oculomotor commands", Nature, 2000, vol. 404, pp. 390-394.

Gregory, et al. "Integration site for Streptomyces phage φBT1 and development of site-specific integrating vectors", Journal of Bacteriology, 2003, vol. 185, No. 17, pp. 5320-5323.

Gulick, et al. "Transfection using DEAE-Dextran" Supplement 40, Current Protocols in Molecular Biology, 1997, Supplement 40, 9.2.1-9.2.10.

Hausser, et al. "Tonic Synaptic Inhibition Modulates Neuronal Output Pattern and Spatiotemporal Synaptic Integration", Neuron, 1997, vol. 19, pp. 665-678.

Kingston et al. "Transfection and Expression of Cloned DNA," Supplement 31, Current Protocols in Immunology, 1999, 10.13.1-10.13.9.

Louis et al. "Cloning and sequencing of the cellular-viral junctions from the human adenovirus type 5 transformed 293 cell line," Virology, 1997, vol. 233, pp. 423-429.

Mortensen et al. "Selection of Transfected Mammalian Cells," Supplement 86, Current Protocols in Molecular Biology, 1997, 9.5.1-09.5.19.

Pear "Transient Transfection Methods for Preparation of High-Titer Retroviral Supernatants" Supplement 68, Current Protocols in Molecular Biology, 1996, 9.1 1 .1-9.1 1 .1 8.

Pouille, et al. "Routing of spike series by dynamic circuits in the hippocampus", Nature, 2004, vol. 429: pp. 717-723.

Rammes, et al., "Synaptic Plasticity in the Basolateral Amygdala in Transgenic Mice Expressing Dominant-Negative cAMP Response Element-binding Protein (CREB) in Forebrain", Eur J. Neurosci, 2000, vol. 12, No. 7, pp. 2534-2546.

Song et al. "Differential Effect of TEA on Long-Term Synaptic Modification in Hippocampal CA1 and Dentate Gyrus in vitro." Neurobiology of Learning and Memory, 2001, vol. 76, No. 3, pp. 375-387.

Song, "Genes responsible for native depolarization-activated K+ currents in neurons," Neuroscience Research, 2002, vol. 42, pp. 7-14.

Wells et al. "Application of Infrared light for in vivo neural stimulation," Journal of Biomedical Optics, 2005, vol. 10(6), pp. 064003-1-064003-12.

Yan et al., "Cloning and Characterization of a Human β, β-Carotene-15, 15'-Dioxygenase that is Highly Expressed in the Retinal Pigment Epithelium", Genomics, 2001, vol. 72: pp. 193-202.

Xiong et al., "Interregional connectivity to primary motor cortex revealed using MRI resting state images", Hum Brain Mapp, 1999, 8(2-3):151-156.

Arenkiel, et al. "In vivo light-induced activation of neural circuitry in transgenic mice expressing Channelrhodopsin-2", Neuron, 2007, 54:205-218.

Milella et al. "Opposite roles of dopamine and orexin in quinpirole-induced excessive drinking: a rat model of psychotic polydipsia" Psychopharmacology, 2010, 211:355-366.

Marin, et al., The Amino Terminus of the Fourth Cytoplasmic Loop of Rhodopsin Modulates Rhodopsin-Transduction Interaction, The Journal of Biological Chemistry, 2000, vol. 275, pp. 1930-1936.

\* cited by examiner

SEQUENCE LISTING

```
<160> NUMBER OF SEQ ID NOS: 4

<210> SEQ ID NO 1
<211> LENGTH: 1302
<212> TYPE: DNA
<213> ORGANISM: Artificial Sequence
<220> FEATURE:
<223> OTHER INFORMATION: rhodopsin/GPCR chimerism

<400> SEQUENCE: 1
atgaacggaa cagagggccc aaacttttac gttcccttct ccaataagac tggggtcgtg      60
agaagcccat ttgaggcgcc tcaatactac cttgctgagc cgtggcagtt ttctatgctc     120
gctgcttaca tgttcttgct gatcatgctg gggttcccta tcaatttcct gacgctgtac     180
gttatagcaa agttcgaacg cctccaaacc gtgttgaact acatactcct taacctcgcg     240
gttgccgacc tcttcatggt tttcgggggt ttcaccacca ccctctacac ctcccttcac     300
ggctacttcg tgttcggccc taccggatgc aatctggaag gttttttcgc aacgctgggg     360
ggggagattg ccctttggag cctggtggtc ttggccatag agaggtacgt ggtggtcaca     420
tccccattca agtaccagag tttgcttaca aagaacaagg ctatcatggg ggtcgccttc     480
```

-continued

```
acatgggtga tggcgctggc ttgcgctgcc ccaccgctgg taggctggtc ccggtatatt    540
ccggagggaa tgcagtgcag ttgtgggatc gactactaca ccccacacga agagactaac    600
aacgagtctt ttgtgattta tatgttcgtg gtccacttca tcatcccccct gatagtgatc   660 tttttctgtt acggcagggt gttccaggtc gccaaaaggc agctccagaa gatcgacaaa    720
agcgaaggcc gctttcacag ccccaatctt ggacaggttg aacaggacgg caggtcaggg    780
cacgggctgc gacgcagttc taagttctgc ctgaaggaac ataaggcctt gagaatggtg    840
atcatcatgg taatcgcctt cctgatatgc tggcttccat acgctggcgt ggctttttat    900
atattcacgc accaggggtc agattttggg cctatcttta tgaccatacc tgctttcttc    960
gctaagacga gtgcggtgta acccagtg atatacatca tgatgaacaa acaattcaga     1020
attgccttcc aggaattgct ctgtctcaga cgcagctctt ccaaagcgta cggaaatggc   1080
tattcatcta acagcaacgg aaagactgat tatatgggcg aagccagtgg ctgccagctg   1140
ggccaggaaa agagagcga gcggctttgt gaagatcccc caggcactga gagcttcgtg    1200
aattgtcagg gaacagttcc gagtctctct cttgattcac agggacgcaa ttgctctacc   1260
aacgacagcc ccctggagac ttcccaggtc gctccggcct aa                     1302
```

<210> SEQ ID NO 2
<211> LENGTH: 434
<212> TYPE: PRT
<213> ORGANISM: Artificial Sequence
<220> FEATURE:
<223> OTHER INFORMATION: rhodopsin/GPCR chimerism

<400> SEQUENCE: 2

```
Met Asn Gly Thr Glu Gly Pro Asn Phe Tyr Val Pro Phe Ser Asn Lys
1               5                   10                  15

Thr Gly Val Val Arg Ser Pro Phe Glu Ala Pro Gln Tyr Tyr Leu Ala
            20                  25                  30

Glu Pro Trp Gln Phe Ser Met Leu Ala Ala Tyr Met Phe Leu Leu Ile
        35                  40                  45

Met Leu Gly Phe Pro Ile Asn Phe Leu Thr Leu Tyr Val Ile Ala Lys
    50                  55                  60

Phe Glu Arg Leu Gln Thr Val Leu Asn Tyr Ile Leu Leu Asn Leu Ala
65                  70                  75                  80

Val Ala Asp Leu Phe Met Val Phe Gly Gly Phe Thr Thr Thr Leu Tyr
                85                  90                  95

Thr Ser Leu His Gly Tyr Phe Val Phe Gly Pro Thr Gly Cys Asn Leu
            100                 105                 110

Glu Gly Phe Phe Ala Thr Leu Gly Gly Glu Ile Ala Leu Trp Ser Leu
        115                 120                 125

Val Val Leu Ala Ile Glu Arg Tyr Val Val Val Thr Ser Pro Phe Lys
    130                 135                 140

Tyr Gln Ser Leu Leu Thr Lys Asn Lys Ala Ile Met Gly Val Ala Phe
145                 150                 155                 160

Thr Trp Val Met Ala Leu Ala Cys Ala Ala Pro Pro Leu Val Gly Trp
                165                 170                 175

Ser Arg Tyr Ile Pro Glu Gly Met Gln Cys Ser Cys Gly Ile Asp Tyr
            180                 185                 190

Tyr Thr Pro His Glu Glu Thr Asn Asn Glu Ser Phe Val Ile Tyr Met
        195                 200                 205

Phe Val Val His Phe Ile Ile Pro Leu Ile Val Ile Phe Phe Cys Tyr
    210                 215                 220
```

-continued

```
Gly Arg Val Phe Gln Val Ala Lys Arg Gln Leu Gln Lys Ile Asp Lys
225                 230                 235                 240

Ser Glu Gly Arg Phe His Ser Pro Asn Leu Gly Gln Val Glu Gln Asp
            245                 250                 255

Gly Arg Ser Gly His Gly Leu Arg Ser Ser Lys Phe Cys Leu Lys
        260                 265                 270

Glu His Lys Ala Leu Arg Met Val Ile Ile Met Val Ile Ala Phe Leu
    275                 280                 285

Ile Cys Trp Leu Pro Tyr Ala Gly Val Ala Phe Tyr Ile Phe Thr His
290                 295                 300

Gln Gly Ser Asp Phe Gly Pro Ile Phe Met Thr Ile Pro Ala Phe Phe
305                 310                 315                 320

Ala Lys Thr Ser Ala Val Tyr Asn Pro Val Ile Tyr Ile Met Met Asn
            325                 330                 335

Lys Gln Phe Arg Ile Ala Phe Gln Glu Leu Leu Cys Leu Arg Arg Ser
        340                 345                 350

Ser Ser Lys Ala Tyr Gly Asn Gly Tyr Ser Ser Asn Ser Asn Gly Lys
        355                 360                 365

Thr Asp Tyr Met Gly Glu Ala Ser Gly Cys Gln Leu Gly Gln Glu Lys
370                 375                 380

Glu Ser Glu Arg Leu Cys Glu Asp Pro Pro Gly Thr Glu Ser Phe Val
385                 390                 395                 400

Asn Cys Gln Gly Thr Val Pro Ser Leu Ser Leu Asp Ser Gln Gly Arg
            405                 410                 415

Asn Cys Ser Thr Asn Asp Ser Pro Leu Thr Glu Thr Ser Gln Val Ala
        420                 425                 430

Pro Ala
```

<210> SEQ ID NO 3
<211> LENGTH: 1485
<212> TYPE: DNA
<213> ORGANISM: Artificial Sequence
<220> FEATURE:
<223> OTHER INFORMATION: rhodopsin/GPCR chimerism

<400> SEQUENCE: 3

```
atgaatggga ccgagggtcc aaattttac gtacccttta gtaacaagac tggcgtggtg      60
cgcagtccat tcgaagcccc acagtactac ctcgcagagc cgtggcaatt ctcaatgctg    120
gccgcttata tgttccttct gattatgctg gggtttccca tcaattttct taccctgtat    180
gtggtagcat gccacagaca tttgcactcc gtattgaatt atattcttct gaacctcgcg    240
gtggcagatc ttttcatggt gttcggcggg tttacgacta ctctgtatac gtccctgcat    300
ggttattttg tgttcgggcc cacaggctgc aacttggaag gcttcttcgc cactcttggc    360
ggtgagatcg ctctttggag cctggtcgtc ctggccatcg agcggtatgt ggtggtgtct    420
tatcctctca gatatcccac catagtgacc cagcggaggg ccattatggg tgtagccttt    480
acctgggtca tggctttggc ctgtgctgct ccccccctgg tgggttggtc ccgctatatt    540
ccagaaggta tgcagtgttc ttgcggaatc gactactata ccccgcacga agagacaaac    600
aacgagtcct tcgtcatata tatgtttgta gtccacttta tcatcccctt gattgttatt    660
ttttttgct atggacgcgt ctacgtcgtg ccaaaaggg agtccagggg cttgaaatct    720
ggactgaaga cagataagag cgattccgag caggtgaccc ttcgcattca taggaagaac    780
gccccagcag gcggaagcgg gatggcatcc gccaagacta aacccacttt tccgtgcgg    840
cttctcaagt tctcccgcga gaaaaggcg gcgcgcatgg tcatcatcat ggttatcgcc    900
```

-continued

```
tttctcattt gctggctgcc ttacgctgga gtcgcgtttt acatcttcac acatcaaggt    960
tctgacttcg gcccaatctt tatgaccatc cctgccttct tcgccaagac ctctgccgtg   1020
tataaccccg ttatctatat tatgatgaac aagcagttcc ggaaggcatt tcagaatgtg   1080
ctgagaatcc aatgcctctg tcggaagcag tctagtaagc atgccctggg gtatactctg   1140
cacccaccca gtcaggctgt agagggccaa cacaaggata tggtgcggat accagtcggt   1200
tccagggaga cattttatcg gattagtaag accgacggag tctgcgagtg gaagttttc   1260 tcttccatgc caggggatc tgcaaggatc acagtttcta aggatcagtc cagctgtacc   1320
acagcccgcg tgcgctccaa atcctttctt caggtctgct gctgtgttgg ccccttcaacc  1380 ccctccctcg ataagaacca tcaggttccc accatcaagg tgcacactat atccttgagc   1440
gaaaacggcg aggaagttga aacttcacag gttgcccccg cctaa                  1485
```

<210> SEQ ID NO 4
<211> LENGTH: 495
<212> TYPE: PRT
<213> ORGANISM: Artificial Sequence
<220> FEATURE:
<223> OTHER INFORMATION: rhodopsin/GPCR chimerism

<400> SEQUENCE: 4

```
Met Asn Gly Thr Glu Gly Pro Asn Phe Tyr Val Pro Phe Ser Asn Lys
1               5                   10                  15

Thr Gly Val Val Arg Ser Pro Phe Glu Ala Pro Gln Tyr Tyr Leu Ala
            20                  25                  30

Glu Pro Trp Gln Phe Ser Met Leu Ala Ala Tyr Met Phe Leu Leu Ile
        35                  40                  45

Met Leu Gly Phe Pro Ile Asn Phe Leu Thr Leu Tyr Val Val Ala Cys
    50                  55                  60

His Arg His Leu His Ser Val Leu Asn Tyr Ile Leu Leu Asn Leu Ala
65                  70                  75                  80

Val Ala Asp Leu Phe Met Val Phe Gly Gly Phe Thr Thr Thr Leu Tyr
                85                  90                  95

Thr Ser Leu His Gly Tyr Phe Val Phe Gly Pro Thr Gly Cys Asn Leu
            100                 105                 110

Glu Gly Phe Phe Ala Thr Leu Gly Gly Glu Ile Ala Leu Trp Ser Leu
        115                 120                 125

Val Val Leu Ala Ile Glu Arg Tyr Val Val Val Ser Tyr Pro Leu Arg
    130                 135                 140

Tyr Pro Thr Ile Val Thr Gln Arg Arg Ala Ile Met Gly Val Ala Phe
145                 150                 155                 160

Thr Trp Val Met Ala Leu Ala Cys Ala Ala Pro Pro Leu Val Gly Trp
                165                 170                 175

Ser Arg Tyr Ile Pro Glu Gly Met Gln Cys Ser Cys Gly Ile Asp Tyr
            180                 185                 190

Tyr Thr Pro His Glu Glu Thr Asn Asn Glu Ser Phe Val Ile Tyr Met
        195                 200                 205

Phe Val Val His Phe Ile Ile Pro Leu Ile Val Ile Phe Phe Cys Tyr
    210                 215                 220

Gly Arg Val Tyr Val Val Ala Lys Arg Glu Ser Arg Gly Leu Lys Ser
225                 230                 235                 240

Gly Leu Lys Thr Asp Lys Ser Asp Ser Glu Gln Val Thr Leu Arg Ile
                245                 250                 255

His Arg Lys Asn Ala Pro Ala Gly Gly Ser Gly Met Ala Ser Ala Lys
            260                 265                 270
```

-continued

```
Thr Lys Thr His Phe Ser Val Arg Leu Leu Lys Phe Ser Arg Glu Lys
        275                 280                 285

Lys Ala Ala Arg Met Val Ile Ile Met Val Ile Ala Phe Leu Ile Cys
    290                 295                 300

Trp Leu Pro Tyr Ala Gly Val Ala Phe Tyr Ile Phe Thr His Gln Gly
305                 310                 315                 320

Ser Asp Phe Gly Pro Ile Phe Met Thr Ile Pro Ala Phe Phe Ala Lys
                325                 330                 335

Thr Ser Ala Val Tyr Asn Pro Val Ile Tyr Ile Met Met Asn Lys Gln
            340                 345                 350

Phe Arg Lys Ala Phe Gln Asn Val Leu Arg Ile Gln Cys Leu Cys Arg
        355                 360                 365

Lys Gln Ser Ser Lys His Ala Leu Gly Tyr Thr Leu His Pro Pro Ser
    370                 375                 380

Gln Ala Val Glu Gly Gln His Lys Asp Met Val Arg Ile Pro Val Gly
385                 390                 395                 400

Ser Arg Glu Thr Phe Tyr Arg Ile Ser Lys Thr Asp Gly Val Cys Glu
                405                 410                 415

Trp Lys Phe Phe Ser Ser Met Pro Arg Gly Ser Ala Arg Ile Thr Val
            420                 425                 430

Ser Lys Asp Gln Ser Ser Cys Thr Thr Ala Arg Val Arg Ser Lys Ser
        435                 440                 445

Phe Leu Gln Val Cys Cys Cys Val Gly Pro Ser Thr Pro Ser Leu Asp
    450                 455                 460

Lys Asn His Gln Val Pro Thr Ile Lys Val His Thr Ile Ser Leu Ser
465                 470                 475                 480

Glu Asn Gly Glu Glu Val Thr Glu Thr Ser Gln Val Ala Pro Ala
                485                 490                 495
```

CELL LINE, SYSTEM AND METHOD FOR OPTICAL CONTROL OF SECONDARY MESSENGERS

RELATED PATENT DOCUMENT

This patent document is the national stage filing under 35 U.S.C. §371 of International Application No. PCT/US2009/045611 filed on May 29, 2009, which claims the benefit, under 35 U.S.C. §119(e), of U.S. Provisional Patent Application Ser. No. 61/057,108 filed on May 29, 2008 and entitled "Cell Line, System and Method for Optical Control of Secondary Messengers;" each of these patent documents is fully incorporated herein by reference.

INCORPORATION-BY-REFERENCE OF MATERIAL SUBMITTED ELECTRONICALLY

Incorporated by reference in its entirety is a computer-readable nucleotide/amino acid sequence listing submitted concurrently herewith, and identified as follows: One 12,342 Byte ASCII (Text) file named "STFD195PCT_ST25.txt" created on Apr. 29, 2009.

FIELD OF THE INVENTION

The present invention relates generally to systems and approaches for generating secondary messengers in response to optical stimulus and more particularly to a cell lines, nucleotide sequences, chimeric proteins, and uses thereof, each relating to the production of secondary messengers in response to light.

BACKGROUND

Guanine nucleotide-binding proteins (G proteins) are believed to alternate between an inactive guanosine diphosphate (GDP) state and an active guanosine triphosphate (GTP) bound state. These two states have been linked to the release of a secondary messenger within a cell. The released secondary messenger can function to regulate downstream cell processes.

Secondary messengers include signaling molecules that are rapidly generated/released. These molecules produce cellular responses by activating effector proteins within the cell. Example cellular signaling systems include the phosphoinositol system, the cyclic adenosine monophosphate (cAMP) system, and the arachidonic acid system.

Changes between the different states of the G proteins can be triggered as a result of proteins called G protein-coupled receptors (GPCRs), G protein-linked receptors (GPLR), seven transmembrane domain receptors (7TM receptors) or heptahelical receptors. This protein family includes a variety of transmembrane receptors. These receptors respond to external stimuli (e.g., light, neurotransmitters, odors or hormones) by activating signal transduction pathways internal to the cell. Specifically, ligands bind and activate the transduction pathways thereby causing the G proteins to alternate states. GPCR-related activity is associated with many diseases, and thus, GPCRs are the target of many pharmaceuticals and treatments.

It is believed that over 30% of all drugs on the market target G-protein coupled receptors (GPCRs) and that many of those drugs relate to the production or inhibition of the secondary messenger cAMP. There is an abundance of pathological processes that directly involve cAMP, including neurophysiological, endocrinological, cardiac, metabolic, and immune diseases. In the study of complex mammalian behaviors, technological limitations have prevented spatiotemporally precise control over intracellular signaling processes. Current chemical-based methods for modulating secondary messenger levels, such as cAMP levels, operate relatively slowly and present problems to study activity on the fast timescales that the body uses in connection with certain tissue, such as in nervous or cardiac tissue. These chemical-methods often lack the speed to probe these fast timescales (e.g., while screening for novel therapeutics).

SUMMARY

The present invention is directed to overcoming the above-mentioned challenges and others related to generation of secondary messengers and related imaging devices and their implementations. The present invention is exemplified in a number of implementations and applications, some of which are summarized below.

Consistent with an embodiment of the present invention, a method is implemented for generating secondary messengers in a cell. A nucleotide sequence for expressing a chimeric light responsive membrane protein (e.g., rhodopsin) is modified with one or more heterologous receptor subunits {e.g., an adrenergic receptor (alpha1, Beta2)}. The light responsive membrane protein is expressed in a cell for producing a secondary messenger in response to light.

Consistent with an embodiment of the present invention, a method is implemented for assessing the efficacy of a putative treatment regimen (e.g., a drug or electrical stimulus or anything that works via these secondary messengers) relating to intracellular messengers. A nucleotide sequence for expressing a chimeric light responsive membrane protein (rhodopsin) is modified with one or more heterologous receptor subunits {e.g., an adrenergic receptor (alpha1, Beta2)}. The light responsive membrane protein is expressed in a cell for producing a secondary messenger in response to light. The protein is exposed to light. The effects of the treatment are assessed.

An embodiment of the present invention is directed toward, a cell expressing a chimeric light responsive membrane protein (rhodopsin) with one or more heterologous receptor subunits {e.g., an adrenergic receptor (alpha1, Beta2)}.

An embodiment of the present invention is directed toward, a nucleotide sequence for expressing a chimeric light responsive membrane protein (rhodopsin) with one or more heterologous receptor subunits {e.g., an adrenergic receptor (alpha1, Beta2)}.

The above summary of the present invention is not intended to describe each illustrated embodiment or every implementation of the present invention. The figures and detailed description that follow more particularly exemplify these embodiments.

BRIEF DESCRIPTION OF THE DRAWINGS

The invention may be more completely understood in consideration of the detailed description of various embodiments of the invention that follows in connection with the accompanying drawings, in which.

Figure 1:
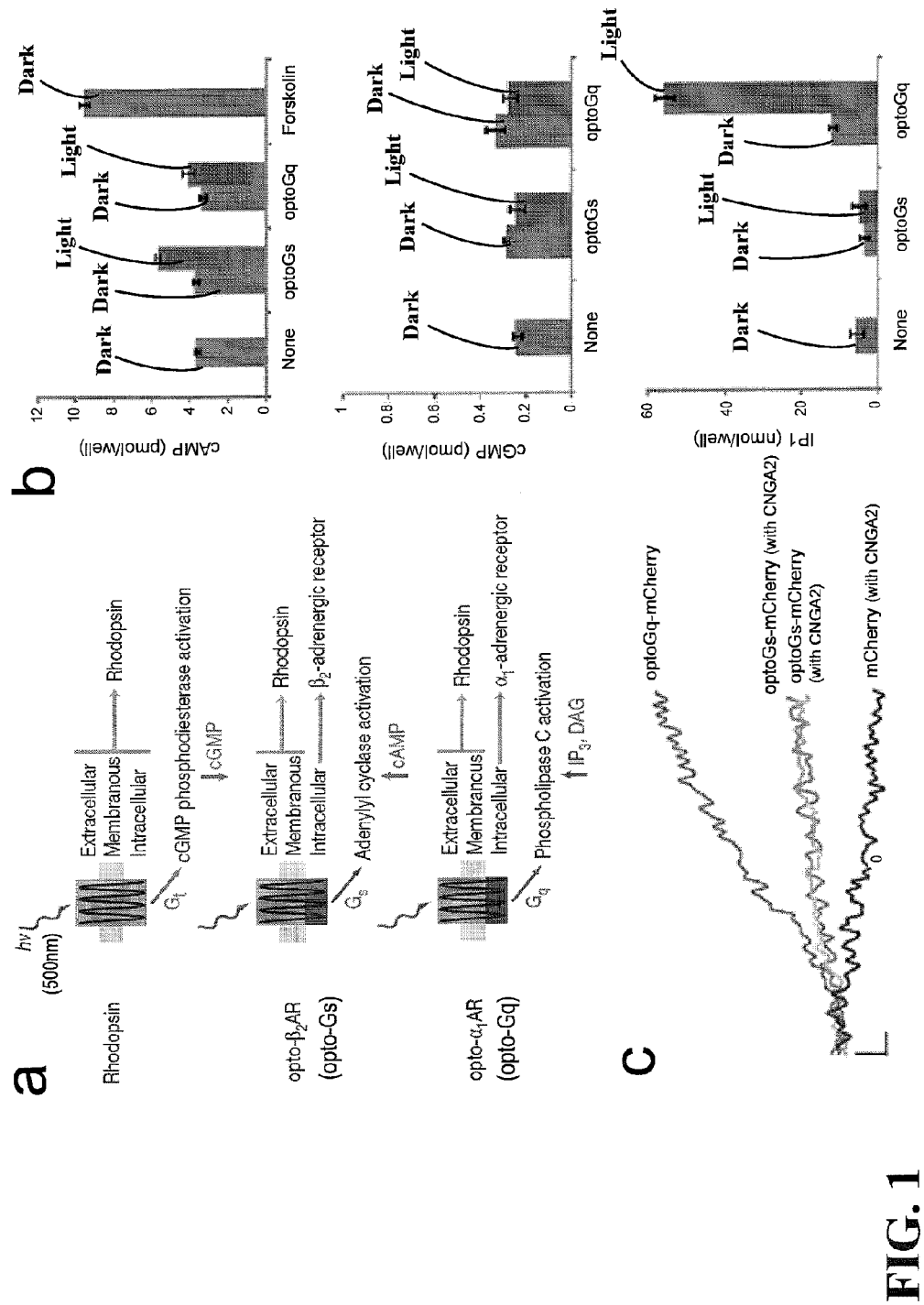
FIG. 1A shows a schematic showing optoGs and optoGq, consistent with example embodiments of the present invention.
FIG. 1B shows Enzyme-Linked Immunosorbent Assay (ELISA) of cAMP, cGMP, and $IP_1$ of cells transfected with either nothing, optoGs, or optoGq, consistent with example embodiments of the present invention.
FIG. 1C shows Ca-imaging of cells transfected with mCherry fusion proteins of optoGs and optoGq, consistent with example embodiments of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The present invention is believed to be useful for enabling practical applications of a variety of optical-based systems and methods, and the invention has been found to be particularly suited for use in systems and methods dealing with optical control of secondary messenger levels within a cell. While the present invention is not necessarily limited to such applications, various aspects of the invention may be appreciated through a discussion of various examples using this context.

Embodiments of the present invention involve a chimeric membrane protein that responds to optical stimulus by causing the release of a secondary messenger within the cell. In a specific instance, the chimeric protein is a combination of a heterologous receptor subunit and a protein that undergoes conformation in reaction to light via photoisomerization and thus is activated by light. Rhodopsins or retinylidene proteins provide an example group of light-responsive proteins that can be modified to include a heterologous receptor subunit.

According to an embodiment of the present invention, a protein believed to contain a seven transmembrane α-helical domain is modified to include a heterologous receptor subunit associated with a secondary messenger. When expressed in a cell membrane, the protein reacts to light by undergoing a conformal change. The conformal change triggers the release/production of the secondary messenger.

Embodiments of the present invention involve a nucleotide sequence for coding a chimeric membrane protein that responds to optical stimulus by causing the release of a secondary messenger within the cell.

Embodiments of the present invention involve a cell that expresses a heterologous and chimeric membrane protein. The chimeric membrane protein responds to optical stimulus by triggering the release of a secondary messenger within the cell. In certain embodiments the expression of the chimeric membrane protein occurs in vivo. In other embodiments expression of the chimeric membrane protein occurs in vitro.

Embodiments of the present invention can implemented for production of any suitable secondary messenger by modifying a Guanine nucleotide-binding protein coupled receptor protein (GPCR) to include the appropriate receptor subunit.

Embodiments of the present invention allow for the use of proteins that respond to a variety of wavelengths and intensities of light.

An embodiment of the present invention involves the use of a chimeric GPCR protein, as disclosed herein, to determine any downstream effect of the secondary messenger activity of interest.

Embodiments of the present invention are directed to expression of a chimeric GPCR protein in a variety of cell types including, but not limited to, mammalian cells, stems cells, plant cells, and unicellular organisms like yeast and *E. coli*.

A specific embodiment of the present invention is related to an optimized expression of a chimeric protein with attached fluorescent proteins for ease of visualization, and optimized use of the modality for studying downstream effects of the secondary messenger activity induced by light.

An embodiment of the present invention is directed to genetically targeting a chimeric GPCR protein, as disclosed herein, to specific cell populations for expression therein. Cell-type specific promoters exist that are selectively expressed in a target cell type (e.g., Synapsin-1 for targeting neurons; Troponin variants for cardiac tissue). Placing these promoters upstream of the chimeric GPCR protein in an expression vector can be used to target expression of the protein to a cell type of interest. This includes inducible, reversible, or otherwise controllable promoter systems such as Tet-response, ER-response, and Cre/Lox systems.

According to an example embodiment of the present invention, a genetically encodeable protein is developed such that, when these are expressed in cell types of interest, cyclic adenosine monophosphate (cAMP) is produced in response to light. This can be useful, for example, to visualize downstream effects on cell physiology including, but not limited to, screening for pharmaceuticals. Other embodiments use a chimeric and heterologous GPCR that results in the release of secondary messengers in response to light. Example secondary messengers include cAMP, cyclic guanosine monophosphate (cGMP), inositol trisphosphate/inositol 1,4,5-trisphosphate/triphosphoinositol ($IP_3$) and arachidonic acid.

Consistent with an embodiment of the present invention, a method is implemented for assessing the efficacy of a putative treatment regimen (e.g., a drug or electrical stimulus or anything that works via these secondary messengers) relating to intracellular messengers. A nucleotide sequence for expressing a chimeric light responsive membrane protein (e.g., rhodopsin) is modified with one or more heterologous receptor subunits {e.g., an adrenergic receptor (alpha1, Beta2)}. The light responsive membrane protein is expressed in a cell for producing a secondary messenger in response to light. The protein is exposed to light. The effects of the treatment are assessed.

The light can be applied according to a desired stimulus profile. In one embodiment the expressed membrane protein responds to light within tens of milliseconds. Thus, the stimulus profile can include a series of light pulses in rapid succession and the resulting effects can be monitored using, for example, $Ca^{2+}$ sensitive dyes.

In one instance, the cell can first be stimulated without the treatment. Once the treatment is administered, the cell can then be stimulated again. The results of each test can be compared to assess the effectiveness of the treatment.

The treatment can include a wide variety of different implementations including, but not limited to, pharmaceuticals, modifications to the cell (genetic or otherwise), physical parameters of the cell (e.g., temperature changes or electrical stimulus) or a treatment regimen applied to an organism.

In one embodiment, the treatment is the optical stimulus of the expressed membrane protein. In such an instance the effectiveness can be measured, for example, by monitoring the symptoms associated with a disorder to be treated.

In another embodiment, the treatment regimen is implemented as part of modeling a disease or disorder. For example, a disease model can be used (cells or animals) and the background/baseline state can be assessed before the protein is expressed and the treatment regimen evaluated.

Experimental results show that optically-evoked cAMP regulation of targeted ion channels can be visualized by transfecting cells with both the cAMP-inducer and a cAMP-targeted cation channel and visualizing resultant activity using $Ca^{2+}$-sensitive dyes. This suite of genetically-encodable, optically-activated modulators of secondary messenger activity can be useful in screening novel therapeutics as well as being a therapeutic modality itself, given the implication of cAMP in numerous diseases states, like ADHD and cardiac channelopathies. The protein can be engineered for use with various other secondary messengers (e.g., $IP_3$), other colors for light activation by engineering the retinal binding site or choosing for the chimera a rhodopsin or cone opsin with a different absorbance/action spectrum, and other downstream effects of the secondary messenger, such as calcium signaling and/or kinase activity.

FIGS. 1A, 1B and 1C show experimental data from optoGs and optoGq, two examples of light-activated inducers of secondary messenger signaling ('optoXRs') that have been developed. These light-activated inducers are a rhodopsin/GPCR chimerism. OptoGq provides light-responsive control of Gq signaling, whereas, OptoGs, provides light-responsive control of Gs signaling.

In both optoGs and optoGq it has been shown that there is negligible difference in baseline cAMP and $IP_3$ levels in darkness and that there is no crossover to other secondary messenger pathways such as cGMP. The increased cAMP levels seen with light stimulation of optoGq is an expected downstream effect of $IP_3$ production.

FIG. 1A shows a schematic of optoGs and optoGq, consistent with example embodiments of the present invention. For each protein, the intracellular loops of rhodopsin are replaced with those of adrenergic proteins normally coupled to either Gs (beta2) or Gq (alpha1). The genetic coding sequences are optimized for expression in human and murine cells. Examples of the resulting sequences include optoGs: Seq. Id. No. 1 and Seq. Id. No. 2; and optoGq: Seq. Id No. 3 and Seq. Id. No 4.

As is appreciated by the skilled artisan, the amino acid sequences of the proteins are presented as non-limiting examples in support of embodiments which extend to variations (e.g., point mutations) in the genetic sequence that otherwise provide consistent, interchangeable or equivalent results.

FIG. 1B shows Enzyme-Linked Immunosorbent Assay (ELISA) of cAMP (top), cGMP (middle), and $IP_1$ (bottom; a degradation product of $IP_3$) of cells transfected with either nothing, optoGs, or optoGq, consistent with an example embodiment of the present invention. The results of FIG. 1B were obtained from cells that were stimulated with 504 nm light (20 nm bandwidth) for one minute per spot or kept in the dark, as indicated.

Stimulation was implemented using an environment-controlled inverted culture microscope (Leica DMI6000B). In the cAMP assay, some cells were treated with 10 uM forskolin for 30 minutes as a saturating, positive control of the assay. OptoGs significantly increased cAMP levels in response to light. No significant baseline increase of cAMP, or deviations of cGMP or $IP_3$ levels with optoGs were found. OptoGq significantly increased IP3 levels in response to light without significantly altering cGMP levels. An increase in cAMP levels with $IP_3$ production is believed to be a consequence of intracellular $Ca^{2+}$ release.

FIG. 1C shows Ca-imaging of cells transfected with mCherry fusion proteins of optoGs and optoGq, consistent with example embodiments of the present invention. To detect cAMP, a cAMP-selective mutant of the cyclic nucleotide gated $Ca^{2+}$ channel CNGA2 was transfected in excess of optoGs. $IP_3$ activates release of intracellular $Ca^{2+}$ stores, thereby providing a reliable signal of Gq activation. A control population was also transfected with mCherry alone with the mutant CNGA2 in excess. Cells were loaded with fura-2 (20-25 minute incubation) and 2 ms exposures of 340 nm and 380 nm were acquired every two seconds. In each of optoGs and optoGq the acquisitions alone were sufficient to yield a Ca signal, while no significant signal was detected in the control population.

FIG. 1 shows data obtained from a specific experimental setup, however, the invention is not so limited. For example, various deliver techniques other than transfecting are contemplated including, but not limited to, viral transduction, ballistic gene delivery (gene gun), and spontaneous nucleic acid uptake.

The base-rhodopsin can be modified for use with any suitable heterologous receptor subunits, such as Gi-coupled receptors like the alpha2-adrenergic receptor or the dopamine D2 receptor or the serotonin 5HT2A receptor; or other Gs- or Gq-coupled receptors like the dopamine D1A receptor or the metabotropic glutamate receptors.

According to one example embodiment, the base-rhodopsin is a protein derived from the bovine *Bos taurus*.

According to one embodiment the base-protein other than the base-rhodopsin mentioned above can also be used and includes various 7-transmembrane proteins, such as the cone opsins (red, green, or blue), rhodopsins of other species, and ligand-gated receptors like the dopamine or serotonin receptors.

Various implementations relate to in vivo applications in mammals These implementations include, but are not limited to, testing and confirming neural circuit and disease models.

Figure 3:
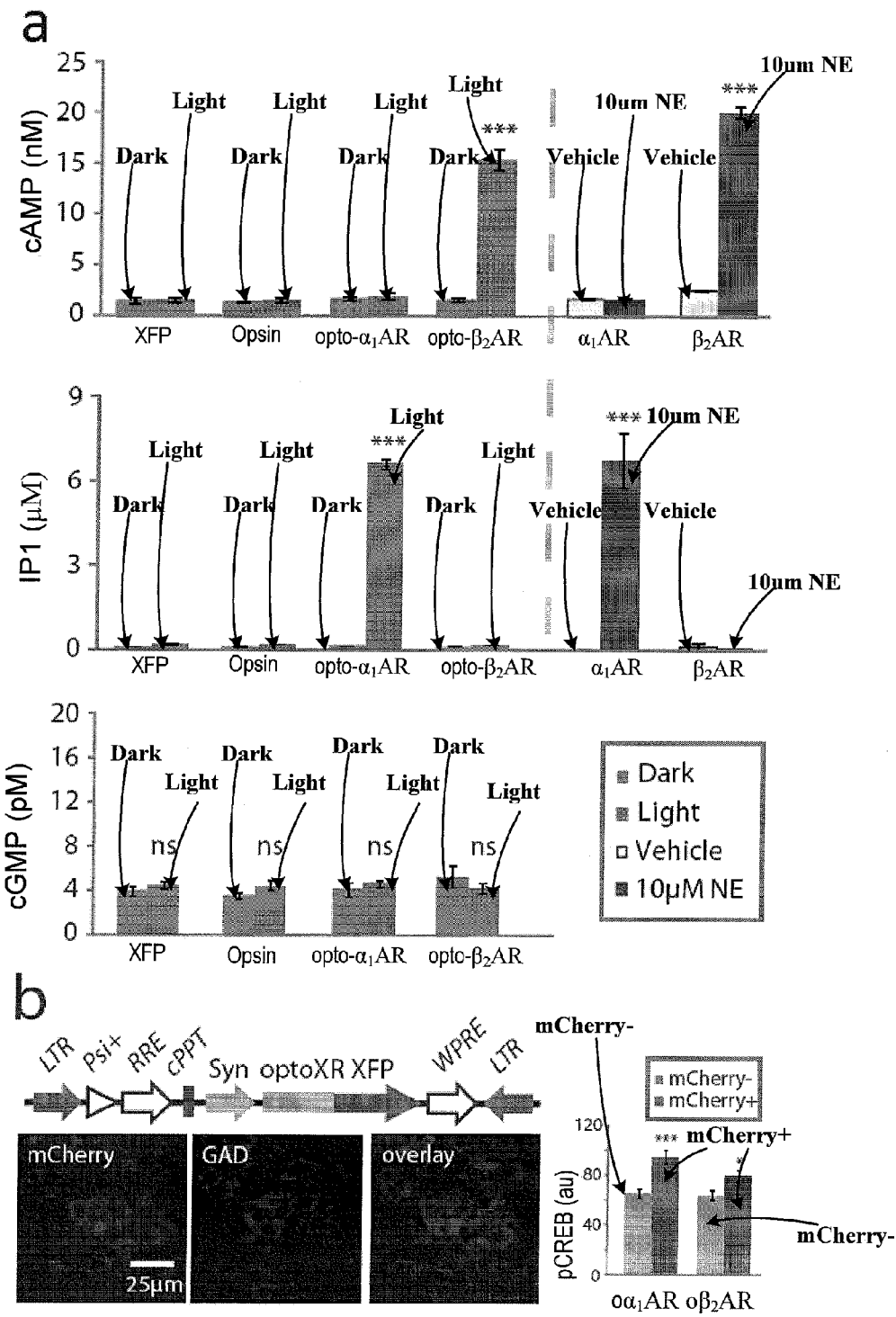
FIG. 3A shows cAMP, $IP_1$ and $IP_3$ levels for HEK cells expressing various constructs, consistent with example embodiments of the present invention.
FIG. 3B shows a lentiviral express vector, GAD immunostaining of opto-$\alpha_1$AR-expressing cells and observed pCREB activation in optoXR-expressing cells (mCherry+) following 10 min optical stimulation, consistent with example embodiments of the present invention.

FIGS. 3A and 3B show experimental data from an in vivo application of optoGs (opto-$\beta_2$AR) and optoGq (opto- $\alpha_1$AR), which are two examples of light-activated inducers of secondary messenger signaling. Aspects of the present invention relate to the use and development of a versatile family of genetically encoded optical tools ('optoXRs') that leverage common structure—function relationships among G-protein-coupled receptors (GPCRs) to recruit and control, with high spatiotemporal precision, receptor-initiated biochemical signaling pathways.

The results shown in FIGS. 3A and 3B relate to two specific optoXRs that selectively recruit distinct, targeted signaling pathways in response to light. The two optoXRs exerted opposing effects on spike firing in nucleus accumbens in vivo, and precisely timed optoXR photostimulation in nucleus accumbens by itself sufficed to drive conditioned place preference in freely moving mice. The optoXR approach allows testing of hypotheses regarding the causal impact of biochemical signaling in behaving mammals, in a targetable and temporally precise manner.

Optical control over intracellular signaling was implemented in mammals, using shared structure—function relationships among GPCRs to develop and express in vivo multiple distinct opsin/GPCR2 chimeras with novel transduction logic that couples signal to effector. Consistent with various implementations, one or more chimeric opsin-receptor proteins are engineered to be functional within mammals in vivo, targetable to specific cells, and responsive to precisely timed light pulses. Such approaches allow for the use of high-speed optical stimulus (and protein response) to test for and characterize intracellular biochemical events at precisely-defined and behaviorally-relevant times. A few non-limiting example implementations include, pulsatile versus tonic modulation, synchrony between different modulatory systems, and other fundamental physiological and pathological processes in defined cell types over a range of timescales.

Mammalian implementations have been successfully implemented. In one example implementation, the intracellular loops of rhodopsin were replaced with those of specific adrenergic receptors by first aligning conserved residues of the Gq-coupled human $\alpha_{1a}$ adrenergic receptor ($\alpha_1$AR) and the Gs-coupled hamster $\beta_2$-adrenergic receptor ($\beta_2$AR) with the Gt-coupled bovine rhodopsin (FIG. 1A). Exchanges of intracellular regions (including carboxy-terminal domains) were engineered for each receptor based on structural models to transfer G-protein coupling from Gt, and optimized each receptor for in vivo expression in mammals Upon activation by varied ligands, the native receptors can explore multiple ensemble states to recruit canonical and non-canonical pathways in a ligand-biased signaling phenomenon. The optoXRs are likely to select a single active ensemble state upon sensing light in a manner dependent on biological context.

Figure 2:
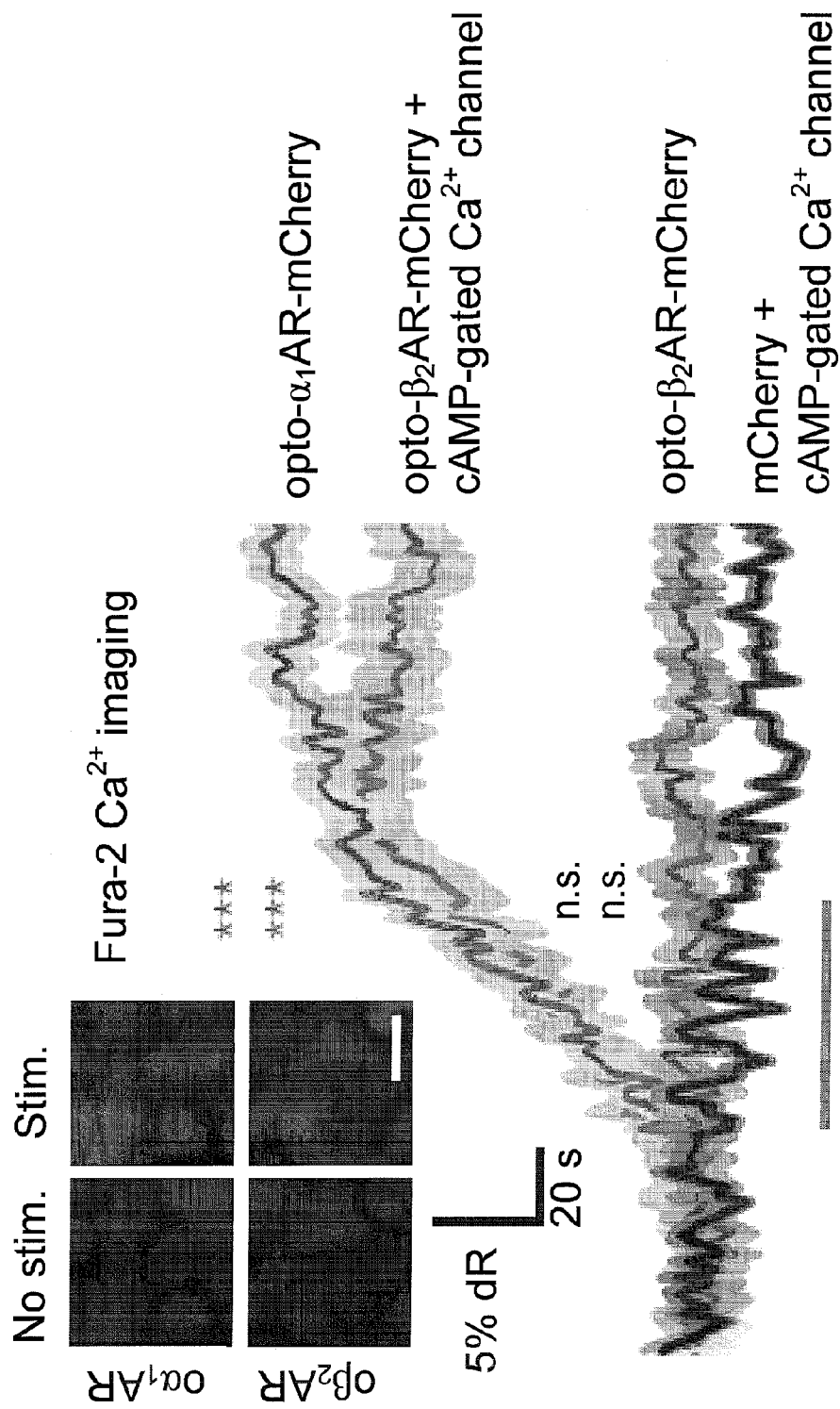
FIG. 2 shows Ca-imaging of cells transfected with mCherry fusion proteins of optoGs and optoGq, consistent with example embodiments of the present invention.

Genes encoding chimeras (opto-$\alpha_1$AR and opto$\beta_2$AR) were fused to a fluorescent protein. Validation of functional optoXR expression, was accomplished through imaged $[Ca^{2+}]_i$ (intracellular calcium concentration) in HEK cells transfected with opto-$\alpha_1$AR alone (expected to recruit$[Ca^{2+}]_i$ via Gq), or with both opto-$\beta_2$AR (expected to recruit cyclic AMP via Gs) and the cAMP-gated $Ca^{2+}$ channel CNGA2-C460W/E583M. Ratiometric $[Ca^{2+}]_i$ imaging demonstrated that 60 s of green light stimulation (504+/−6 nm, 7 mW mm$^{-2}$) was sufficient to drive prominent $[Ca^{2+}]_i$ signals downstream of either optoXR but not in control conditions (FIG. 2), revealing functional expression. To test specificity of the signaling controlled by each optoXR, transduced HEK cells were illuminated with 3 mW mm$^{-2}$ 504+/−6 nm light for 60 s and then lysed and analyzed for levels of cGMP, cAMP and $IP_1$ (a degradation product of $IP_3$) via immunoassays. The canonical pattern was as expected for opto-$\beta_2$AR corresponding to its molecular design, as optical stimulation yielded significant production of cAMP in opto-$\beta_2$AR-expressing cells (FIG. 3A, top), comparable to that achieved with pharmacological stimulation of the wild-type $\beta_2$AR and without recruitment of $IP_3$ (FIG. 3A, middle), $[Ca^{2+}]_i$ (FIG. 2), or substantial dark activity. In contrast, optical stimulation yielded significant upregulation of $IP_3$ signaling in opto-$\alpha_1$AR-expressing cells (FIG. 3A, middle), comparable to levels induced by pharmacological stimulation of the wild-type $\alpha_1$AR. Together with the $[Ca^{2+}]_i$ elevations (FIG. 2), these data reveal the pattern expected for Gq recruitment, a pattern not seen in opto-$\beta_2$AR-expressing cells (FIG. 3A, top). Optical stimulation of cells expressing either construct was unable to modulate cGMP levels (FIG. 3A, bottom), further indicating the signaling specificity of the chimeric proteins. Similar assays revealed that the optoXRs retain an action spectrum close to that of native rhodopsin, are able to integrate signals over a range of biologically suitable light fluxes, and can activate non-canonical pathways to a similar extent as wild-type receptors, as for p42/p44-MAPK signaling.

OptoXR performance in intact neural tissue has been tested, including whether or not supplementation of retinal cofactors was necessary. In one such test, lentiviral vectors carrying the optoXR fusion genes under control of the synapsin-I promoter (to target biochemical modulation to local neurons rather than other potentially Gs/Gq-responsive cellular tissue elements such as glia and endothelial cells; FIG. 3B, top left) were stereotactically injected into the nucleus accumbens of adult mice. This strategy targets biochemical modulation to neurons with somatodendritic compartments in accumbens (~95% GABAergic medium spiny neurons, without further subtype specificity; FIG. 3B, left) and excludes fibers of passage or afferent presynaptic terminals as these lentiviruses do not transduce cells via axons. Two weeks after transduction, acute coronal slices of accumbens were prepared in artificial cerebrospinal fluid, optically stimulated for 10 min, and immediately fixed and stained for Ser 133-phosphorylated CREB (pCREB), a biochemical integrator of both cAMP and $Ca^{2+}$-coupled signaling cascades. Without supplementation of exogenous retinoids, significantly elevated pCREB was observed in the optoXR-expressing populations (FIG. 3B, right) and not in non-illuminated tissue.

Figure 4:
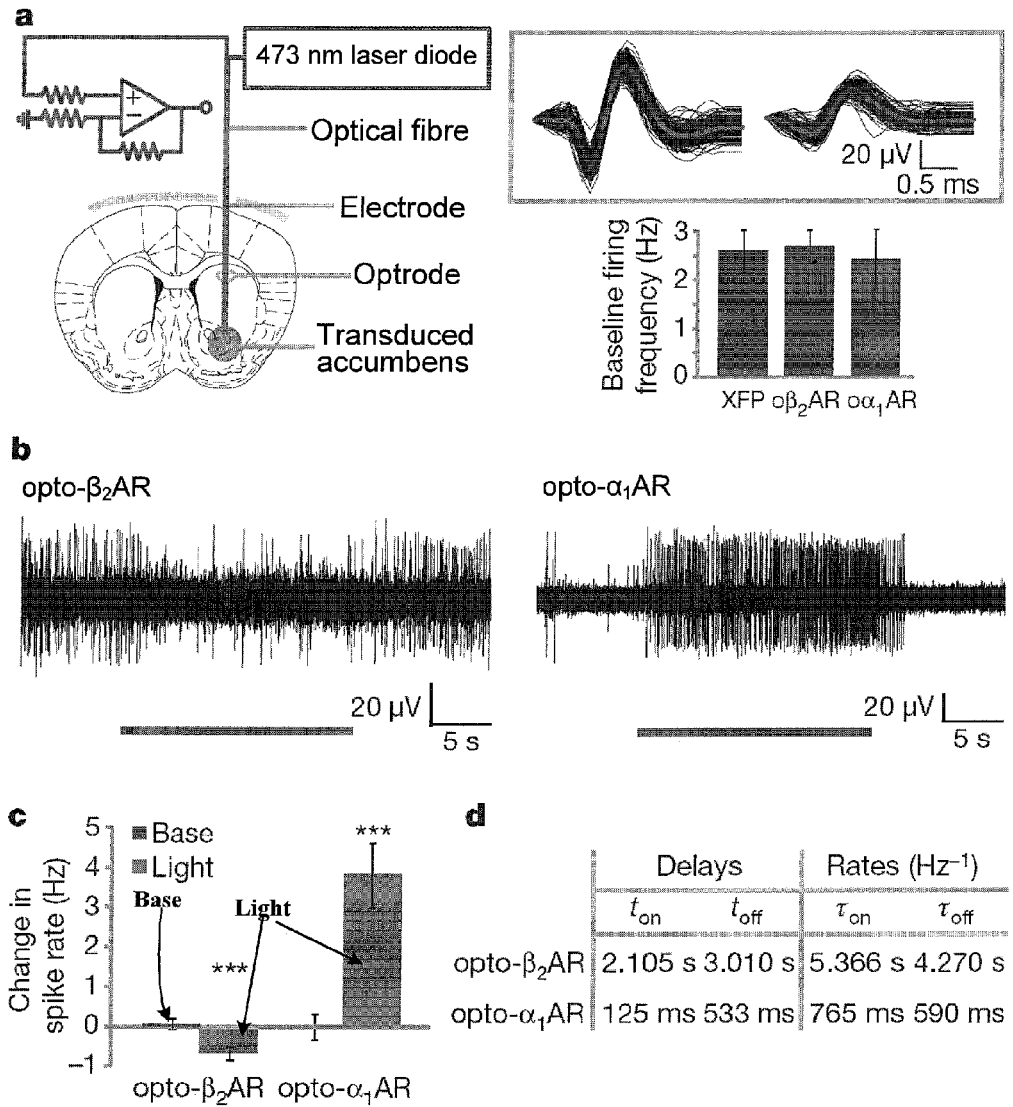
FIG. 4A shows optrode targeting of transduced accumbens, spike waveforms and baseline firing rates for indicated constructs, consistent with example embodiments of the present invention.
FIG. 4B shows in vivo optrode recordings with light stimulation, consistent with example embodiments of the present invention.
FIG. 4C shows change in spiking frequency with light versus baseline, consistent with example embodiments of the present invention.
FIG. 4D shows firing rate change kinetics, consistent with example embodiments of the present invention.

The functional consequences of optoXR activation on accumbens local electrical activity was determined by recording multi-unit in vivo neuronal firing with an optrode targeted to transduced accumbens (FIG. 4A). No significant differences in baseline firing rates were observed in the dark with either construct (FIG. 4A, bottom right). Optical stimulation resulted in decreased network firing in opto-$\beta_2$AR-expressing accumbens (left trace in FIG. 4B illustrates effect kinetics; summary data shown in FIGS. 4C and 4D respectively), in agreement with previous pharmacological studies targeting Gs. Optical stimulation increased firing in opto-$\alpha_1$AR-expressing accumbens (FIG. 4B right; FIG. 4C, 4D). Spike frequency histograms showed that the kinetics of optoXR effects on firing rates was consistent with biochemical rather than electrical initiation of the signal (FIG. 4D). These electrophysiological data, in combination with the earlier biochemical validations, support that optoXRs can be functionally expressed in vivo, to permit differential photoactivatable control of intracellular cascades and to modulate network physiology.

Figure 5:
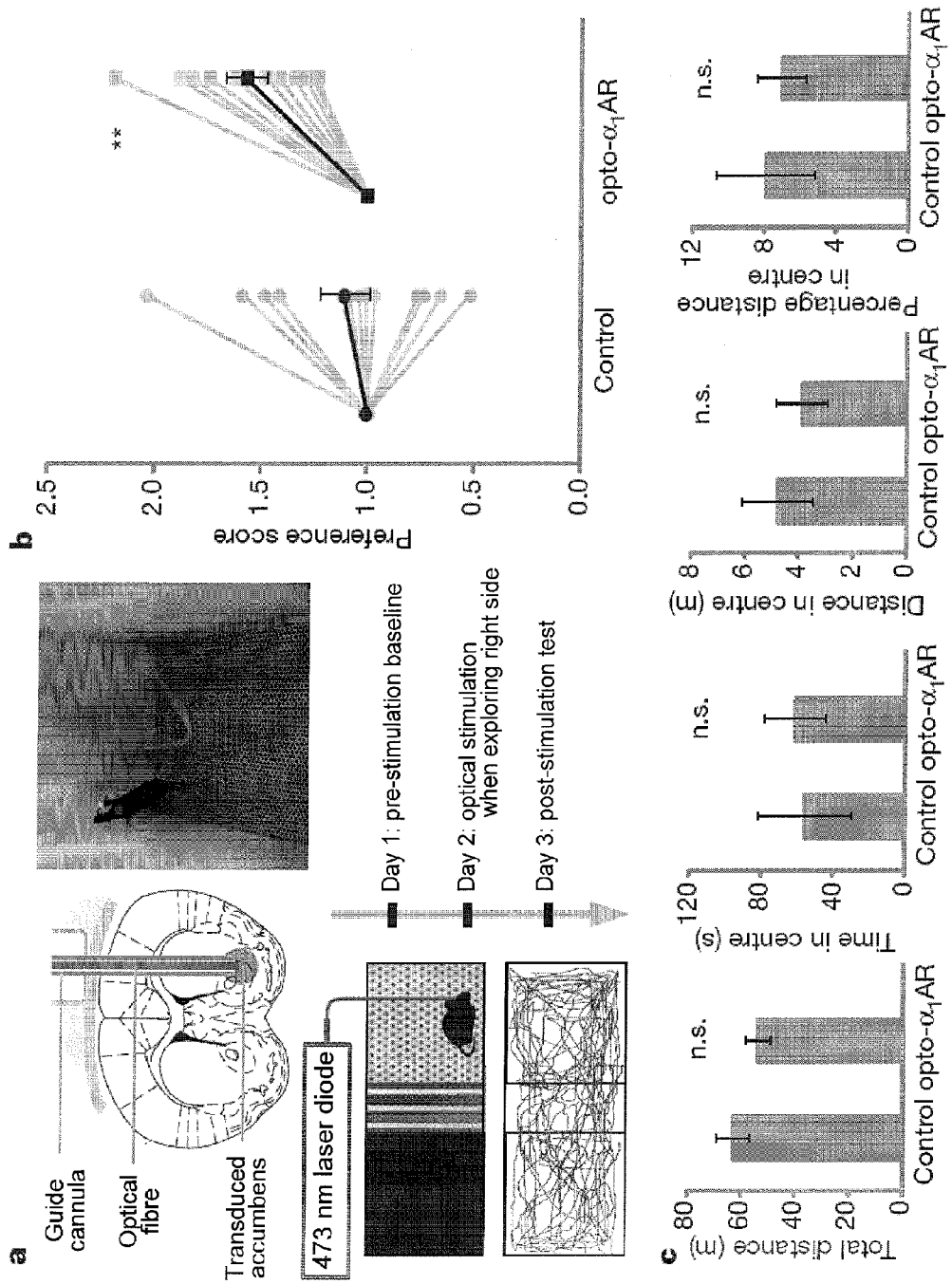
FIG. 5A shows stereotactic targeting of a transduced region, a freely moving mouse with implanted fiber optics, a schematic of place preference apparatus and test and a trace of a freely exploring mouse, consistent with example embodiments of the present invention.
FIG. 5B shows preferences for control and opto-$\alpha_1$AR, consistent with example embodiments of the present invention.
FIG. 5C shows results of total distance for various open field tests; consistent with example embodiments of the present invention.

In one implementation, optogenetics were used to assess the ability of precisely timed optoXR stimulation to modulate behavior in freely moving mice. Portable solid-state light delivery was combined with transgenic expression of optoXRs to optically control intracellular signaling within accumbens neurons in the temporally precise manner used for operant behavior (FIG. 5A). Confocal analysis revealed expression to be limited to local accumbens neurons; in particular no labeling was observed in afferent fibers, in distant regions projecting to accumbens, in glia, or in surrounding regions. Optical stimulation was targeted to transduced accumbens as part of a three-day operant conditioned place preference assay (FIG. 5A). On each day of the test, animals were allowed to freely explore the place preference apparatus (FIG. 5A, bottom). On day 1, animals freely explored the apparatus without optical stimulation. On day 2, whenever the animal freely entered the designated conditioned chamber, a laser-diode-coupled optical fiber registered to the transduced region delivered light pulses at 10 Hz to approximate the likely intensity of monoaminergic input during strong reward. Path tracing revealed that the flexible optical fiber approach allowed full and unimpeded exploration of all chambers (FIG. 5A, bottom). On day 3, animals again freely explored the apparatus without optical stimulation, and the time spent in the conditioned chamber was quantified by two independent, blinded scorers. Notably, animals expressing opto-$\alpha_1$AR showed a robust increase in preference for the conditioned side of the apparatus following optical stimulation (FIG. 5B). This effect of temporally precise biochemical modulation was reproducible across two separate cohorts of opto-$\alpha_1$AR animals (n=5-6, P<0.05, Student's t-test for each cohort for time in conditioned chamber; n=11, P<0.01 for the total population), whereas the other opsin genes, opto-$\beta_2$AR and ChR2, appeared less effective in driving preference. The effect of opto-$\alpha_1$AR stimulation in accumbens neurons was specific to reward-related behavior and did not extend to direct modulation of anxiety-related behaviors or locomotor activity, as identical optical stimulation delivered to a cohort of the same animals in an open field test revealed no significant effect on distance travelled or preference for wall proximity (FIG. 5C).

A specific and non-limiting implementation that is consistent with the above experiments is now described. In vivo recording and analysis was performed using optrodes consisting of a multi-mode optical fiber 200 mm in diameter (Thorlabs) coupled to a recording electrode (1MV tungsten, A-M Systems) with an electrode/fiber tip-to-tip distance of 200-400 mm were lowered into the transduced accumbens (electrode tip 4.8-5.2 mm below bregma) of mice placed in a stereotactic frame (David Kopf Instruments) and anaesthetized under isoflurane. Light from a 473 nm diode laser (CrystaLaser) was delivered through the fiber. Electrical signals were bandpass filtered and amplified (0.3-1 kHz, 1800 Microelectrode AC Amplifier, A-M Systems) and analyzed with pClamp 10.0 (Molecular Devices). Spikes were detected by threshold and individually confirmed by inspection.

Behavioral analysis was performed using optical stimulation that was applied through an optical fiber (200 mm diameter, Thor Labs) coupled to a 473 nm blue diode laser (CrystaLaser) and registered with a cannula targeting accumbens (0-100 mm from tip). Light was delivered with 50 ms pulse width for optoXRs via a function generator (Agilent 33220A). Place preference was conducted in a standard apparatus (SD Instruments) with walls between chambers removed to permit free exploration. Data were analyzed from video for amount of time spent in each chamber by two independent, blinded observers using a custom tallying script run in MATLAB (Mathworks). For open field tests, animals were placed in a square open field measuring 40340 cm; light stimulation was delivered with the same parameters as for place preference experiments. Videos were analyzed using automated software (Viewpoint), for total time and distance in the central 15315 cm square versus the outer annulus (remainder of the field).

Statistical analysis, where indicated, was performed using two-tailed Student's t-tests (calculated in Microsoft Excel) or one-way ANOVA with Tukey post-hoc tests (GraphPad Prism) were used. All summary bar graphs are presented as mean+/−s.e.m., with significance denoted as follows: *$P<0.05$, $P<0.01$, *$P<0.001$.

Further details supporting the surprising results and effectiveness of various embodiments of the present invention can be found in *Temporally precise in vivo control of intracellular signalling*, Raag D. Airan, et al., Nature 458, 1025-1029 (23 Apr. 2009), which is fully incorporated herein by reference.

The following description provides details for specific and non-limiting method that is consistent with an embodiment of the present invention. Numerous variations of this methodology are envisioned and within the scope of the present invention.

Vector Construction

Mammalian codon optimized sequences of opto-$\alpha_1$AR and opto-$\beta_2$AR (amino acid sequences in FIG. 1A) were synthesized and cloned into pcDNA3.1, and fused to the N-terminus of mCherry or YFP (with its start codon deleted) using the NotI site. The linker between the optoXR and mCherry/YFP is 5' GCGGCCGCC 3'. Lentiviral vectors containing Synapsin I optoXR mCherry were constructed by cloning the transgene for each optoXR mCherry into the AgeI and EcoRI sites of the pLenti SynapsinI hChR2 mCherry WPRE vector.

Lentiviral Production

High titer lentivirus was produced. Briefly, HEK 293FT cells were plated to 90% confluence in a 4-layer cell factory (Nunc) cultured with DMEM containing 10% FBS. Cells were co-transfected with 690 μg of the lentiviral vector described above and two helper plasmids (690 μg of pΔC-MVR8.74 and 460 μg of pMD2.G). Media was changed at 15 h post transfection. At 24 h post transfection, media was changed with 200-220 mL of serum free UltraCULTURE (Cambrex) containing 5 mM sodium butyrate. At 40 h post transfection, the culture supernatant, now containing viruses, was spun at 1000 rpm for 5 min to remove cellular debris and then filtered using a 0.45 μm low-protein-binding filter flask. The clarified supernatant was then ultra centrifuged for 2 h at 55,000 g using an SW 28 rotor (Beckman) to precipitate the virus. After centrifugation, supernatant was discarded and the resultant viral pellet was dissolved in a total of 100 μL of cold (4° C.) PBS. The resuspended virus was centrifuged for 5 min at 7000 rpm to remove remaining cellular and viral debris. Aliquots were frozen at −80° C. until further use.

Animal Surgery and Behavior

Female C57BL/6 mice, 10-12 weeks old, were housed and handled according to the Laboratory Vertebrate Animals protocol of Stanford University. Virus solution was delivered to the right nucleus accumbens as follows. Animals were anaesthetized under isoflurane and fur was sheared from the top of the head. While under isoflurane anesthesia, the head of the animal was placed in a stereotactic frame (David Kopf Instruments). A midline scalp incision was made and a ~1 mm diameter craniotomy was drilled 1.10 mm anterior, and 1.45 mm lateral to bregma. A beveled 33 gauge needle (NanoFil, World Precision Instruments) pre-loaded with virus was then lowered into the accumbens (needle tip at 4.70-4.80 mm ventral to bregma) and 1.0 μL of virus was injected at 100 nL/min using an automated syringe pump (NanoFil, World Precision Instruments). Following injection, 3-5 min was allowed for tissue relaxation and fluid diffusion before retraction of the needle. For animals targeted for acute slice or in vivo recording experiments, the craniotomy was filled with dental cement (Lang Dental) and the incision was closed using VetBond (3M). For animals targeted for behavioral analysis, cannulas (C316G, cut 4.5 mm below the pedestal; PlasticsOne) were placed with the pedestal flush to the skull. Cannulae were secured using Metabond (Parkell) and dental cement (Lang Dental). Following drying of VetBond or cement, animals were removed from the frame and allowed to recover for at least one week before further manipulation. Control animals for behavioral experiments underwent the same manipulations (surgery, cannula implantation, light stimulation) as experimental animals, and were injected with vehicle (PBS) alone instead of virus. For place preference experiments, animals that did not show a baseline preference for either side chamber (>70% or <10%) or for the central chamber (>40%) were admitted into the study; >90% of all animals met these criteria for an unbiased, balanced place preference design.

Acute Slice Preparation

Animals were anaesthetized under isoflurane and decapitated using surgical shears (Fine Science Tools). Coronal, 275 µm-thick slices containing accumbens were cut and stored in a cutting solution containing 64 mM NaCl, 2.5 mM KCl, 1.25 mM $NaH_2PO_4$, 25 mM $NaHCO_3$, 10 mM glucose, 120 mM sucrose, 0.5 mM $CaCl_2$ and 7 mM $MgCl_2$ (equilibrated with 95% $O_2$/5% $CO_2$). Following slicing, slices were incubated in the cutting solution at 32-35° C. for 30 min and then at room temperature until experimentation. For ex vivo optoXR stimulation, slices were loaded on the stage of an upright microscope (BX51W, Olympus) and perfused with an artificial cerebrospinal fluid containing 124 mM NaCl, 3 mM KCl, 1.25 mM $NaH_2PO_4$, 26 mM $NaHCO_3$, 10 mM glucose, 2.4 mM $CaCl_2$, and 1.3 mM $MgCl_2$ (equilibrated with 95% $O_2$/5% $CO_2$). Light from a 300 W Lambda DG-4 (Sutter) was passed through a 473 nm±20 nm bandpass filter (Semrock) and applied to the slices using a 4× objective (0.28 NA) for 10 min followed immediately by fixation for later analysis.

Signaling Validation Assays

HEK293FT cells (Invitrogen) were transfected using Lipofectamine 2000 (Invitrogen) in 24 well plates and changed to serum-free medium 4-6 hrs post-transfection. For $Ca^{2+}$ imaging, cells plated on matrigel-coated coverslips were loaded with 5 µg/ml fura-2 AM in F-127 Pluronic/DMSO (Probes) in Tyrode containing 1 µM ATR, at 37° C. and 5% atmospheric $CO_2$ for 20-25 min. Following loading, coverslips were imaged at 340 nm/380 nm on an Olympus BX51W using Metafluor (Axon Instruments) controlling a 300 W Lambda DG-4 (Sutter). For immunoassays, 18-24 hrs after transfection, 1 µM ATR and 50 mM LiCl (to prevent $IP_1$ degradation) were added and plates transferred to an environmentally-controlled microscope (Leica DMI6000; 37° C., 5% atmospheric $CO_2$). 5 regions/well were optically stimulated for 1 min each (Sutter 300 W Lambda DG-4; Semrock 504/12 nm bandpass filter; 10× 0.30 NA objective); 3 wells/condition. Following incubation (cAMP/cGMP: 20 min; $IP_1$: 1 hr), cells were lysed and analyze by HTRF (CisBio) and a Biotek Synergy4 reader.

Immunohistochemistry and Confocal Analysis

Following in vivo stimulation, mice were transcardially perfused with ice-cold 4% paraformaldehyde (PFA) in PBS (pH 7.4) 90 min after termination of stimulation. Brains were removed and fixed overnight in 4% PFA and then equilibrated in 30% sucrose in PBS. Coronal, 40 µm-thick sections were cut on a freezing microtome and stored in cryoprotectant at 4° C. until processed for immunohistochemistry. Free-floating sections were washed in PBS and then incubated for 30 min in 0.3% Tx100 and 3% normal donkey serum (NDS). For acute slice experiments, immediately following stimulation the 275 µm-thick slices were fixed for 1 hr in ice-cold 4% PFA and incubated with 0.5% Tx100 and 3% NDS. For MAPK assays, immediately following HEK293 cell stimulation, coverslips were fixed for 15 min, incubated with 0.6% $H2O2$ and then permeabilized with 0.1% Tx100 in 3% NDS. Primary antibody incubations were conducted overnight in 0.01% Tx100 and 3% NDS for mouse anti-GAD67 1:500, Millipore, Billerica, Mass.; rabbit anti-cfos 1:500, Calbiochem, San Diego, Calif.; rabbit anti-phospho-CREB Ser133 1:500, Millipore. Sections were washed and incubated with secondary antibodies (1:1000) conjugated to either FITC or Cy5 (Jackson Laboratories, West Grove, Pa.) for 3 hrs at room temperature. Following 20 min incubation with DAPI (1:50,000) sections were washed and mounted on microscope slides with PVD-DABCO. The remaining overnight primary antibody incubations (rabbit anti-phosphoErk1/2; anti-phospho-MARK p38 1:500, Promega, Madison, Wis.; mouse monoclonal anti-dopamine D1 receptor 1:50, Chemicon; rabbit polyclonal anti-dopamine D2 receptor 1:50, Millipore; goat polyclonal anti-choline acetyltransferase 1:200, Millipore) were followed by incubation with biotinylated secondary antibody (1:500, Jackson Laboratories), avidin-biotin-horseradish peroxidase treatment (ABC kit, Vector Labs, Burlingame, Calif.), and TSA detection (Perkin Elmer, Shelton, Conn.) according to manufacturer's instructions.

Confocal fluorescence images were acquired on a Leica TCS SP5 scanning laser microscope using a 20×/0.70 NA or a 40×/1.25 NA oil immersion objective. Four serial stack images per condition were acquired within a 500 µm region beneath the cannula tract. DAPI staining was used to delineate nuclei for determination of the mean pixel intensity of cfos or pCREB immunoreactivity using Volocity (Improvision) software. Positive or pCREB-active cells were identified by intensity threshold, and image acquisition and analysis were performed blind to the experimental conditions.

TABLE S1

Raw numerical pCREB intensities (au) for data represented in FIG. 3B. Mean and SEM in bold for each subgroup; p-values for two-tailed t-test of subgroup versus control in italics.

|  | opto-$\alpha_1$AR | | opto-$\beta_2$AR | |
|---|---|---|---|---|
| mCherry | − | + | − | + |
| Mean | 65.326 | 97.95309 | 63.6385 | 82.83284 |
| SEM | 3.758281 | 7.199024 | 3.847409 | 6.907057 |
| p-value vs. mCherry− | | *0.000272* | | *0.019559* |

TABLE S2

Raw numerical baseline firing rates (Hz) for data presented in FIG. 4A. Mean and SEM in bold for each subgroup; p-values for t-test of subgroup versus in italics.

|  | XFP | o$\alpha_1$AR | o$\beta_2$AR |
|---|---|---|---|
| Mean | 2.596154 | 2.439357 | 2.687798 |
| SEM | 0.436406 | 0.603845 | 0.346556 |
| p-value vs XFP | | *0.834496* | *0.869791* |

TABLE S3

Raw numerical changes in firing rate (Hz) for data presented in FIG. 4C calculated within the baseline itself ('Base') and between the baseline and the light stimulation periods ('Light').

|  | opto-$\beta_2$AR | | Opto-$\alpha_1$AR | |
| --- | --- | --- | --- | --- |
|  | Base | Light | Base | Light |
| Mean | 0.061788 | −0.68113 | −0.01287 | 3.816198 |
| SEM | 0.134665 | 0.162402 | 0.336387 | 0.812251 |
| p-value vs Base |  | 0.000861 |  | 0.000239 |

Accordingly, embodiments of the present invention relate to optogenetic control of intracellular signaling and are useful for temporally precision while operating in vivo within behaving mammals, while displaying extremely low dark activity, and recruiting the complex fabric of multiple signaling molecules downstream of native receptors, thereby unifying in a single technology many of the individual positive aspects of other approaches. Similar embodiments directly probe the causal significance of seven-transmembrane-dependent signaling pathways triggered by other modulators, including myriad neurotransmitters and endocrine hormones. Other embodiments use an optoXR approach in ways that extend beyond excitable cells to capitalize upon the versatile integration of fiber-optic depth targeting with optogenetically targeted photosensitivity. One such embodiment relates to probing causal significance of temporally precise biochemical signaling in diverse non-excitable tissues.

Embodiments of the present invention relate to considerations of the phenomenon of ligand-biased signaling, wherein varied ligands can stabilize ensemble receptor conformational states and thereby bias the intracellular action of the receptor in coupling to alternative transduction cascades. The optoXRs are used to induce these alternative cascades to similar levels as with pharmacological manipulation (for example, opto-$\beta_2$AR can induce similar changes in MAPK activation compared with native ligand acting on the wild-type $\beta_2$AR); however, individual optoXRs may not always be found to permit control of all of the conformational states that contribute to ligand biased signaling Retinal-based tools can be particularly useful due to the presence of the endogenous chromophore in mammalian tissues, and the extremely low activity in the dark. Optogenetics can take the form of diverse effectors linked to fast, single-component retinal-binding modules, capitalizing on the temporal precision of optics.

Embodiments of the present invention use optoXR methods to complement microbial opsin strategies, providing another dimension of fast, targetable cellular control operative in behaving mammals.

Consistent with another embodiment of the present invention, wavelength-shifted versions of the optoXRs, based on known opsin genes with different action spectra, are used. Such optoXRs can be particularly useful for providing separable channels of biochemical and electrical control.

Variants of the specific protein sequences discussed herein are consistent with embodiments of the present invention. Some variants are greater than about 75% homologous to these protein sequences, while others are greater than about 80%, 85% or 90%. In some embodiments the homology will be as high as about 93 to about 95 or about 98%. The compositions of the present invention include the protein and nucleic acid sequences provided herein including variants which are more than about 50% homologous to the provided sequence up to and including 100% homologous.

The various embodiments discussed herein could be integrated with fast circuit readout technologies for increasingly sophisticated interrogation and reverse engineering of neural circuitry, both in normal operation and in disease states.

The various embodiments described above are provided by way of illustration only and should not be construed to limit the invention. Based on the above discussion and illustrations, those skilled in the art will readily recognize that various modifications and changes may be made to the present invention without strictly following the exemplary embodiments and applications illustrated and described herein. For instance, such changes may include variations of the secondary messenger produced. Such modifications and changes do not depart from the true spirit and scope of the present invention, which is set forth in the following claims.

What is claimed is:

1. A method for generating secondary messengers in a cell, the method comprising:
   expressing in the cell a chimeric light-responsive fusion protein comprising a light-responsive rhodopsin-based membrane protein and a heterologous alpha-1 adrenergic receptor, wherein said expression provides for production of a secondary messenger in response to light, and wherein the chimeric light-responsive fusion protein comprises an amino acid sequence having at least 85% amino acid sequence identity to the amino acid sequence set forth in SEQ ID NO:4;
   wherein the cell expresses a secondary messenger-targeted cation channel that is responsive to the secondary messenger; and
   visualizing resultant activity using a cation-sensitive dye.

2. The method of claim 1, wherein the secondary messenger is inositol trisphosphate/inositol 1,4,5-trisphosphate/triphosphoinositol ($IP_3$).

3. The method of claim 1, wherein the step of expressing is accomplished in vivo.

4. The method of claim 1, wherein the step of expressing is accomplished in vitro.

5. The method of claim 1, further including the step of optically stimulating the expressed light responsive membrane protein.

6. A method for assessing the efficacy of a treatment regimen relating to intracellular messengers, the method comprising:
   expressing a chimeric light-responsive fusion protein comprising a light-responsive rhodopsin-based membrane protein and a heterologous alpha-1 adrenergic receptor in a mammalian cell, wherein said expression provides for production of a secondary messenger in response to light, and wherein the chimeric light-responsive fusion protein comprises an amino acid sequence having at least 85% amino acid sequence identity to the amino acid sequence set forth in SEQ ID NO:4;
   wherein the cell expresses a secondary messenger-targeted cation channel that is responsive to the secondary messenger;
   exposing the chimeric light-responsive fusion protein to light; and
   assessing the effects of the treatment by visualizing resultant activity using a cation-sensitive dye.

7. The method of claim 1, wherein the amino acid sequence has at least 90% amino acid sequence identity to the amino acid sequence set forth in SEQ ID NO:4.

8. The method of claim 1, wherein the chimeric light-responsive fusion protein is encoded by a nucleotide sequence that is operably linked to a cell type-specific promoter.

9. The method of claim 1, wherein the cell is a mammalian cell.

10. The method of claim 1, wherein the cell is a neuron.

11. The method of claim 8, wherein the cell type-specific promoter is a neuron-specific promoter.

12. The method of claim 10, wherein the promoter is a synapsin-1 promoter.

13. The method of claim 5, wherein the step of optically stimulating the expressed light responsive chimeric membrane protein comprises applying light through an optical fiber.

14. The method of claim 5, wherein the step of optically stimulating the expressed light responsive chimeric membrane protein comprises applying a pulsatile optical stimulus.

15. The method of claim 1, wherein the amino acid sequence has at least 95% amino acid sequence identity to the amino acid sequence set forth in SEQ ID NO:4.

16. The method of claim 6, wherein the secondary messenger is inositol trisphosphate/inositol 1,4,5-trisphosphate/triphosphoinositol ($IP_3$).

17. The method of claim 6, wherein the amino acid sequence has at least 90% amino acid sequence identity to the amino acid sequence set forth in SEQ ID NO:4.

18. The method of claim 6, wherein the amino acid sequence has at least 95% amino acid sequence identity to the amino acid sequence set forth in SEQ ID NO:4.

19. The method of claim 6, wherein the chimeric light-responsive fusion protein is encoded by a nucleotide sequence that is operably linked to a cell type-specific promoter.

20. The method of claim 6, wherein the cell is a neuron.

21. The method of claim 19, wherein the cell type-specific promoter is a neuron-specific promoter.

22. The method of claim 21, wherein the promoter is a synapsin-1 promoter.

* * * * *